United States Patent
Kurisu et al.

(10) Patent No.: US 12,420,415 B2
(45) Date of Patent: Sep. 23, 2025

(54) RECOMMENDED LOAD DETERMINING DEVICE, CAPABILITY PARAMETER ESTIMATION MODEL TRAINING DEVICE, METHOD, AND PROGRAM

(71) Applicant: OMRON Corporation, Kyoto (JP)

(72) Inventors: Takanori Kurisu, Kyoto (JP); Satoshi Yase, Kyoto (JP); Masamune Nakayama, Kyoto (JP)

(73) Assignee: OMRON Corporation, Kyoto (JP)

( * ) Notice: Subject to any disclaimer, the term of this patent is extended or adjusted under 35 U.S.C. 154(b) by 202 days.

(21) Appl. No.: 18/265,053

(22) PCT Filed: Sep. 15, 2021

(86) PCT No.: PCT/JP2021/033879
§ 371 (c)(1),
(2) Date: Jun. 2, 2023

(87) PCT Pub. No.: WO2022/130714
PCT Pub. Date: Jun. 23, 2022

(65) Prior Publication Data
US 2024/0017409 A1    Jan. 18, 2024

(30) Foreign Application Priority Data
Dec. 18, 2020 (JP) ................................ 2020-210721

(51) Int. Cl.
*B25J 9/16*    (2006.01)

(52) U.S. Cl.
CPC ............. *B25J 9/1664* (2013.01); *B25J 9/163* (2013.01)

(58) Field of Classification Search
CPC .. A61B 5/11; A61B 5/22; A61B 5/224; A63B 24/0062; A63B 24/0075;
(Continued)

(56) References Cited

U.S. PATENT DOCUMENTS 9,622,685 B2 *   4/2017   Wisbey ................. A61B 5/1118
10,065,074 B1 *  9/2018   Hoang ....................... G01P 1/02
(Continued)

FOREIGN PATENT DOCUMENTS

| CN | 107773961 A | 3/2018 |
|---|---|---|
| CN | 107803010 A | 3/2018 |

(Continued)

OTHER PUBLICATIONS

Extended European Search Report dated Oct. 18, 2024, issued in corresponding European Patent Application No. 21906079.5.
(Continued)

*Primary Examiner* — Joshua Lee
(74) *Attorney, Agent, or Firm* — Morgan, Lewis & Bockius LLP

(57) ABSTRACT

In a recommended load determining device (10) utilizing an estimation model (18) that outputs a parameter related to a capability of a user calculated based on load data expressing a load imparted to the user and on motion data expressing motion of a single motion unit of the user under the load, an acquisition section (12) acquires load data expressing a load imparted to a target user who is a target for determining a recommended load, and motion data expressing motion of a single motion unit of the target user under the load, and a determination section (20) determines recommended load data expressing a recommended load for the target user based on a parameter related to the capability of the target user as output from the estimation model (18) by inputting the acquired load data and the acquired motion data into the estimation model (18).

23 Claims, 37 Drawing Sheets

(58) Field of Classification Search
CPC . A63B 69/00; A63B 2102/16; A63B 2220/30; A63B 2220/806; B25J 9/163; B25J 9/1664; G06N 3/09; G06V 40/23; G09B 19/0038; G16H 20/30; G16H 30/40; G16H 40/63; G16H 50/20; G16H 50/70
See application file for complete search history.

(56) References Cited

U.S. PATENT DOCUMENTS

| | | | | |
|---|---|---|---|---|
| 10,112,075 | B2* | 10/2018 | Wisbey | G16H 40/63 |
| 10,129,628 | B2* | 11/2018 | Wisbey | H04R 1/1041 |
| 11,996,001 | B2* | 5/2024 | Otsuki | G06N 3/08 |
| 2016/0023047 | A1* | 1/2016 | Wisbey | A61B 5/02427 |
| | | | | 434/247 |
| 2017/0216671 | A1* | 8/2017 | Wisbey | A61B 5/02438 |
| 2018/0369637 | A1* | 12/2018 | Hoang | G09B 19/003 |
| 2021/0005106 | A1* | 1/2021 | Otsuki | G05B 13/0265 |
| 2022/0110548 | A1* | 4/2022 | Radwin | A61B 5/0022 |
| 2023/0270352 | A1* | 8/2023 | Zelik | A61B 5/6823 |
| | | | | 600/595 |

FOREIGN PATENT DOCUMENTS

| | | |
|---|---|---|
| FR | 2875140 A1 | 3/2006 |
| JP | H11-235401 A | 8/1999 |
| JP | 2010-205043 A | 9/2010 |
| JP | 2014-104265 A | 6/2014 |
| JP | 2018-055611 A | 4/2018 |
| JP | 2018-175670 A | 11/2018 |
| JP | 2019-107235 A | 7/2019 |
| JP | 2020-199049 A | 12/2020 |
| WO | 2018/194082 A1 | 10/2018 |

OTHER PUBLICATIONS

International Search Report issued in corresponding International Patent Application No. PCT/JP2021/033879 dated Nov. 16, 2021.
Written Opinion issued in corresponding International Patent Application No. PCT/JP2021/033879 dated Nov. 16. 2021.
Office Action issued in corresponding Chinese Patent Application No. 202180081640.8, dated May 20, 2025.

* cited by examiner

FIG.2

| USER NO. | 1 | | | 2 | | |
|---|---|---|---|---|---|---|
| ATTEMPT NO. | 1 | ... | 100 | 1 | ... | 100 |
| LOAD DATA | L11 | ... | L1100 | L21 | ... | L2100 |
| MOTION DATA | A11 | ... | A1100 | A21 | ... | A2100 |
| RESULT DATA | R11 | ... | R1100 | R21 | ... | R2100 |
| CAPABILITY PARAMETER | C1 | | | C2 | | |

| | | | | | | 214 |
|---|---|---|---|---|---|---|
| USER NO. | 1 | | | 2 | | ... |
| ATTEMPT NO. | 1 | ... | 100 | 1 | ... | 100 | ... |
| LOAD DATA (HIT SPEED) | 3 m/s | ... | 8.5 m/s | 4.5 m/s | ... | 7.0 m/s | ... |
| MOTION DATA (SKELETON INFORMATION) | SWING 1_1 | ... | SWING 1_100 | SWING 2_1 | ... | SWING 2_100 | ... |
| RESULT DATA (BALL RETURN ERROR) | 0.1m | ... | 0.5m | 0.1m | ... | 0.5m | ... |
| CAPABILITY PARAMETER (MAXIMUM RETURNABLE BALL SPEED) | 8 m/s | | | 3 m/s | | | ... |

FIG.11

| | USER NO. | 1 | | | 2 | | |
|---|---|---|---|---|---|---|---|
| | ATTEMPT NO. | 1 | ... | 100 | 1 | ... | 100 |
| | LOAD DATA (PITCHING SPEED) | 120km/h | ... | 150km/h | 130km/h | ... | 157km/h |
| | MOTION DATA (SKELETON INFORMATION) | SWING 1_1 | ... | SWING 1_100 | SWING 2_1 | ... | SWING 2_100 |
| | RESULT DATA (BATTING RESULT) | SAFE HIT | ... | EASY FLY | SAFE HIT | ... | EASY FLY |
| | CAPABILITY PARAMETER (MAXIMUM SAFE-HITTABLE BALL SPEED) | 130km/h | | | 145km/h | | |

| USER NO. | 1 | | | 2 | | | ... |
|---|---|---|---|---|---|---|---|
| ATTEMPT NO. | 1 | ... | 100 | 1 | ... | 100 | ... |
| LOAD DATA (RUNNING BELT SPEED) | 0.2 m/s | ... | 0.5 m/s | 0.2 m/s | ... | 0.47 m/s | ... |
| MOTION DATA (SKELETON INFORMATION) | WALK 1_1 | ... | WALK 1_100 | WALK 2_1 | ... | WALK 2_100 | ... |
| RESULT DATA (CENTER OF GRAVITY VARIATION) | 20cm | ... | 30cm | 10cm | ... | 15cm | ... |
| CAPABILITY PARAMETER (MAXIMUM WALKABLE SPEED) | 0.8 m/s | | | 1 m/s | | | ... |

| USER NO. | 1 | | | | 2 | | | ... |
|---|---|---|---|---|---|---|---|---|
| ATTEMPT NO. | 1 | ... | 100 | | 1 | ... | 100 | ... |
| LOAD DATA — HIT SPEED | 3 m/s | ... | 8.5 m/s | | 4.5 m/s | ... | 7.0 m/s | ... |
| LOAD DATA — BALL SPIN | 30 rad/s | ... | -50 rad/s | | 25 rad/s | ... | -40 rad/s | ... |
| LOAD DATA — RELATIVE POSITION | 0.5m | ... | -0.5m | | 0.2m | ... | -0.4m | ... |
| MOTION DATA (SKELETON INFORMATION) | SWING 1_1 | ... | SWING 1_100 | | SWING 2_1 | ... | SWING 2_100 | ... |
| RESULT DATA (BALL RETURN ERROR) | 0.3m | ... | 0.8m | | 0.2m | ... | 0.5m | ... |
| CAPABILITY PARAMETER (HEAT MAP) | (heat map: BALL RETURN RATE, RELATIVE POSITION, HIT SPEED, BALL SPIN) | | | | (heat map: BALL RETURN RATE, RELATIVE POSITION, HIT SPEED, BALL SPIN) | | | ... |

| ATTEMPT NO. | 1 | 2 | ... |
|---|---|---|---|
| RESULT DATA (BALL RETURN ERROR) | 0.5m | 0.7m | ... |

| USER NO. | JOINT TIME SWING | JOINT 1X COORDINATE | | | JOINT 1Y COORDINATE | | | JOINT 1Z COORDINATE | | | ... | JOINT n X COORDINATE | | | JOINT n Y COORDINATE | | | JOINT n Z COORDINATE | | |
|---|---|---|---|---|---|---|---|---|---|---|---|---|---|---|---|---|---|---|---|---|
| | | t0 | ... | tf | t0 | ... | tf | t0 | ... | tf | | t0 | ... | tf | t0 | ... | tf | t0 | ... | tf |
| 1 | SWING 1_1 | | | | | | | | | | | | | | | | | | | |
| 1 | ... | | | | | | | | | | | | | | | | | | | |
| 1 | SWING 1_100 | | | | | | | | | | | | | | | | | | | |
| 2 | SWING 2_1 | | | | | | | | | | | | | | | | | | | |
| 2 | ... | | | | | | | | | | | | | | | | | | | |
| 2 | SWING 2_100 | | | | | | | | | | | | | | | | | | | |
| ... | ... | | | | | | | | | | | | | | | | | | | |

FIG.36

| USER NO. | MAIN COMPONENT / SWING | P1 | P2 | ... | Ps |
|---|---|---|---|---|---|
| 1 | SWING 1_1 | | | | |
| | ⋮ | | | | |
| | SWING 1_100 | | | | |
| 2 | SWING 2_1 | | | | |
| | ⋮ | | | | |
| | SWING 2_100 | | | | |
| ... | ... | | | | |

FIG.37

| USER NO. | FEATURE VALUE / SWING | ELBOW HEIGHT | ... | SMOOTHNESS OF TRAJECTORY |
|---|---|---|---|---|
| 1 | SWING 1_1 | | | |
| | : | | | |
| | SWING 1_100 | | | |
| 2 | SWING 2_1 | | | |
| | : | | | |
| | SWING 2_100 | | | |
| ... | ... | | | |

RECOMMENDED LOAD DETERMINING DEVICE, CAPABILITY PARAMETER ESTIMATION MODEL TRAINING DEVICE, METHOD, AND PROGRAM

TECHNICAL FIELD

The present disclosure relates to a recommended load determining device, a capability parameter estimation model training device, a recommended load determining method, and a recommended load determining program.

BACKGROUND ART

Hitherto there has been a proposal for technology that, when a person is performing exercise, work, rehabilitation, or the like using a machine, automatically determines a control value for the machine based on biometric information of the person and the like.

For example, a control device is proposed for controlling a drive section of a production line according to an experience level of a worker (see Patent Document 1: Japanese Patent Application Laid-Open (JP-A) No. 2018-55611). The control device described in Patent Document 1 includes a storage section for storing biometric information associated with experience level for each experience level of worker. The control device acquires biometric information that has been measured for a worker, and compares a feature value of the biometric information acquired during work against a feature value of biometric information for each experience level in the storage section. Then based on the results of this comparison, the control device determines which experience level corresponds to the acquired biometric information, and determines a control value of the drive section based on the determined experience level.

Moreover, for example, there is a proposal for a rehabilitation support device that enables setting of an appropriate difficulty level (see Patent Document 2: JP-A No. 2019-107235). The device described in Patent Document 2 includes a reception section, an acquisition section, a computation section, and an output control section. The reception section receives input of a first index value of brain activity measured by fMRI, a first success rate for a rehabilitation task, and a first difficulty level of the rehabilitation task for a subject who is the target of rehabilitation. The acquisition section acquires correlations between a second index value of brain activity measured by fMRI, a second success rate for a rehabilitation task, and a second difficulty level of a rehabilitation task for plural people who performed the rehabilitation. The computation section computes a third difficulty level of rehabilitation to be executed by the subject based on an input and the correlations, and the output control section outputs the third difficulty level.

Moreover, there is a proposal for a motor capability evaluation device for evaluating a motor capability that does not impart restrictions to a test subject, has few failed evaluations, and that does not need special biometric information sensors (see Patent Document 3: JP-A No. H11-235401). The device described in Patent Document 3 increases an exercise load intensity stepwise from P1 to P2, and according to this load increase, lowers a rotation speed resulting from a motor action on a rotating machine from R1 by $\Delta R$. Moreover, as the test subject subsequently attempts to return to the original rotation speed R1, this device finds a time ½tf to return the rotation speed by ½ $\Delta R$ according to the motor action to raise the rotation speed, and uses this time ½tf as an evaluation of motor capability.

SUMMARY OF INVENTION

Technical Problem

For example, in cases in which a load is imparted to a user who is asked to execute a given motor task, preferably an appropriate load is imparted so as to improve the skill of the user at the motor task. However, in the technology described in Patent Document 1, fluctuations in the biometric information are not able to be discriminated between those resulting from changes in load imparted to a person by a robot, and those resulting from progress made be the person themselves. Namely, whether or not the skill of the user is improving is not able to be ascertained. This means that the technology described in Patent Document 1 has an issue in that an appropriate load so as to improve the skill of the user for the given motor task is not able to be imparted.

Moreover, the technology described in Patent Document 2 is technology to appropriately adjust a difficulty level of a rehabilitation task to match a patient. The technology of Patent Document 3 is technology to perform evaluation of motor capability. This means that all these technologies have the issue described above, that is they are not applicable to imparting an appropriate load so as to improve the skill of the user for a given motor task.

In consideration of the above circumstances, an object of the present disclosure is to determine a load advantageous to skill improvement of a user when a load is imparted to the user to execute a motor task.

Solution to Problem

In order to achieve the above object, a recommended load determining device of the disclosure utilizes an estimation model that outputs a parameter related to a capability of a user calculated based on load data expressing a load imparted to the user and on motion data expressing motion of a single motion unit of the user under the load. The recommended load determining device is configured including an acquisition section that acquires load data expressing a load imparted to a target user who is a target for determining a recommended load, and motion data expressing motion of a single motion unit of the target user under the load, and a determination section that determines recommended load data expressing a recommended load for the target user based on a parameter related to the capability of the target user as output from the estimation model by inputting the acquired load data and the acquired motion data into the estimation model.

The recommended load determining device of the disclosure utilizes the estimation model that outputs the parameter related to the capability of a user calculated based on the load data expressing the load imparted to the user and on the motion data expressing motion of a single motion unit of the user under the load. In the recommended load determining device the acquisition section acquires the load data expressing a load imparted to the target user who is the target for determining the recommended load and the motion data expressing the motion of the single motion unit of the target user under the load, and the determination section determines the recommended load data expressing the recommended load for the target user based on the parameter related to the capability of the target user as output from the estimation model by inputting the acquired load data and the acquired motion data into the estimation model.

This thereby enables a load to be determined that is advantageous to skill improvement of the user when a motor task imparting the load to the user is executed.

Moreover, the motion data may be displacement data of a particular location of the user or of an implement held when the user is performing the motion, muscle activity quantity data of the user, or differentiated data or integrated data of the displacement data or the muscle activity quantity data. The displacement data of the particular location of the user may be time series data of skeleton information of the user.

The parameter related to the capability output by the estimation model may be load limit data expressing a value of the load at a maximum burden for the user from within a range of values of the load for one load item when an expectation of success for the motion is higher than a prescribed standard, and the determination section may determine the load limit data for the target user as the recommended load data.

The parameter related to the capability output by the estimation model may be a parameter expressing a relationship between the load and a success expectation value for the motion, and the determination section may determine the recommended load data based on the parameter related to the capability for the target user.

The parameter expressing a relationship between the load and the success expectation value for the motion for the target user may be a parameter to identify a graph expressing a relationship between a value of the load for one load item and the success expectation value, and the determination section may determine, as the recommended load data, load limit data expressing a value of the load for a maximum burden for the target user from within a range of values of the load in the graph for which the expectation of success is higher than a prescribed standard.

The parameter expressing the relationship between the load and the success expectation value for the motion for the target user may be a parameter to identify a heat map expressing a relationship between values of the load for plural load items and the success expectation value, and the determination section may determine, as the recommended load data, a set of values of load in the heat map for which the success expectation is higher than a prescribed standard.

The determination section may output data to display a visualization of the heat map.

The determination section may be configured so as to be able to utilize a comparison heat map, may create a relative strength map that identifies a relative strength range that is a range of a set of values of the load for which the success expectation of the target user is higher in a comparison to the comparison heat map or create a relative weakness map that identifies a relative weakness range that is a range of a set of values of the load for which the success expectation of the target user is lower in a comparison to the comparison heat map, and may determine a set of values of load in the relative strength range or in the relative weakness range as the recommended load data.

The comparison heat map may be prepared for separate levels of the user, and the determination section may utilize the comparison heat map for the user at a level equivalent to a level of the target user or at a level that is above the level of the target user and that is a level nearest to the level of the target user.

The acquisition section may further acquire an instruction of strength or weakness for the target user, and the determination section may create the relative strength map in cases in which the strength instruction was acquired and may create the relative weakness map in cases in which the weakness instruction was acquired.

The determination section may output data to display a visualization of at least one out of the relative strength map or the relative weakness map.

The estimation model may be prepared for each type of the motion, the acquisition section may acquire an instruction for one of the types from the target user, and the determination section may determine the recommended load data using the estimation model corresponding to the instructed type.

The acquisition section may acquire plural sets of a set of the load data and the motion data, and the determination section may input the estimation model with load data resulting from averaging the plural load data and with motion data resulting from averaging the plural motion data.

The acquisition section may acquire plural sets of a set of the load data and the motion data, and the determination section may average a parameter related to the capability obtained by each set of the load data and the motion data being input to the estimation model, and may determine the recommended load data based on the averaged parameter.

The acquisition section may acquire plural sets of a set of the load data and the motion data, and the determination section may compute plural recommended load data based on a parameter related to the capability obtained by each of the sets of the load data and the motion data being input to the estimation model, and may further finally determine the recommended load data by averaging the plural recommended load data.

The acquisition section may acquire a set of the load data and the motion data and a measured parameter related to an actual motion result corresponding to the set, and the determination section may determine the recommended load data so as to have a smaller burden on the target user in cases in which a capability of the target user as evaluated by the acquired measured parameter is lower than a capability of the target user as evaluated by the parameter as output from the estimation model.

The determination section may output the recommended load data to a load imparting device that imparts the load to the target user as data for controlling the load imparting device. The determination section may output data to display a latest of the recommended load data at a prescribed time interval.

The recommended load determining device of the disclosure may be configured so as to include a training section that generates the estimation model by learning correspondences of the load data and the motion data with respect to a parameter related to a capability of the user as calculated based on the load data and the motion data.

To generate the estimation model the training section may employ the motion data that has been compressed such that a difference between a number of dimensions of the load data and a number of dimensions of the motion data is within a prescribed range.

A capability parameter estimation model training device of the disclosure is configured including an acquisition section that acquires load data expressing a load imparted to a user, motion data indicating motion of a single motion unit of the user under the load, and result data accompanying the motion, and a training section that learns correspondences of the load data and the motion data with respect to a parameter related to a capability of the user as calculated based on the load data and the result data so as to generate an estimation model that outputs a parameter related to a capability of a target user, who is a target for determining a recommended load, on being input with the load data and the motion data for the target user.

A recommended load determining method of the disclosure is a method including preparing an estimation model that outputs a parameter related to a capability of a user calculated based on load data expressing a load imparted to the user and on motion data expressing motion of a single motion unit of the user under the load, an acquisition section acquiring load data expressing a load imparted to a target user who is a target for determining a recommended load and on motion data expressing motion of a single motion unit of the target user under the load, and a determination section determining recommended load data expressing a recommended load for the target user based on a parameter related to the capability of the target user as output from the estimation model by inputting the acquired load data and the acquired motion data into the estimation model.

A recommended load determining program of the disclosure is a program to cause a computer to function as a recommended load determining device that utilizes an estimation model that outputs a parameter related to a capability of a user calculated based on load data expressing a load imparted to the user and on motion data expressing motion of a single motion unit of the user under the load. The program causes the computer to function as an acquisition section that acquires load data expressing a load imparted to a target user who is a target for determining a recommended load, and motion data expressing motion of a single motion unit of the target user under the load, and a determination section that determines recommended load data expressing a recommended load for the target user based on a parameter related to the capability of the target user as output from the estimation model by inputting the acquired load data and the acquired motion data into the estimation model.

The recommended load determining device, capability parameter estimation model training device, method, and program of the disclosure enables determination of a load advantageous to skill improvement of a user when a load is imparted to the user to execute a motor task.

BRIEF DESCRIPTION OF DRAWINGS

FIG. 2 is a diagram illustrating an example of a training data DB of the first exemplary embodiment.

FIG. 8 is a diagram illustrating an example of a training data DB of a second exemplary embodiment.

FIG. 11 is a diagram illustrating an example of another training data DB.

FIG. 12 is a diagram illustrating an example of another training data DB.

FIG. 13 is a diagram illustrating an example of a training data DB of the third exemplary embodiment.

FIG. 27 is a diagram illustrating an example of an actual score DB.

FIG. 35 is a diagram to explain an example of dimension compression of motion data.

FIG. 36 is a diagram to explain an example of dimension compression of motion data.

FIG. 37 is a diagram to explain an example of dimension compression of motion data.

DESCRIPTION OF EMBODIMENTS

Figure 1:
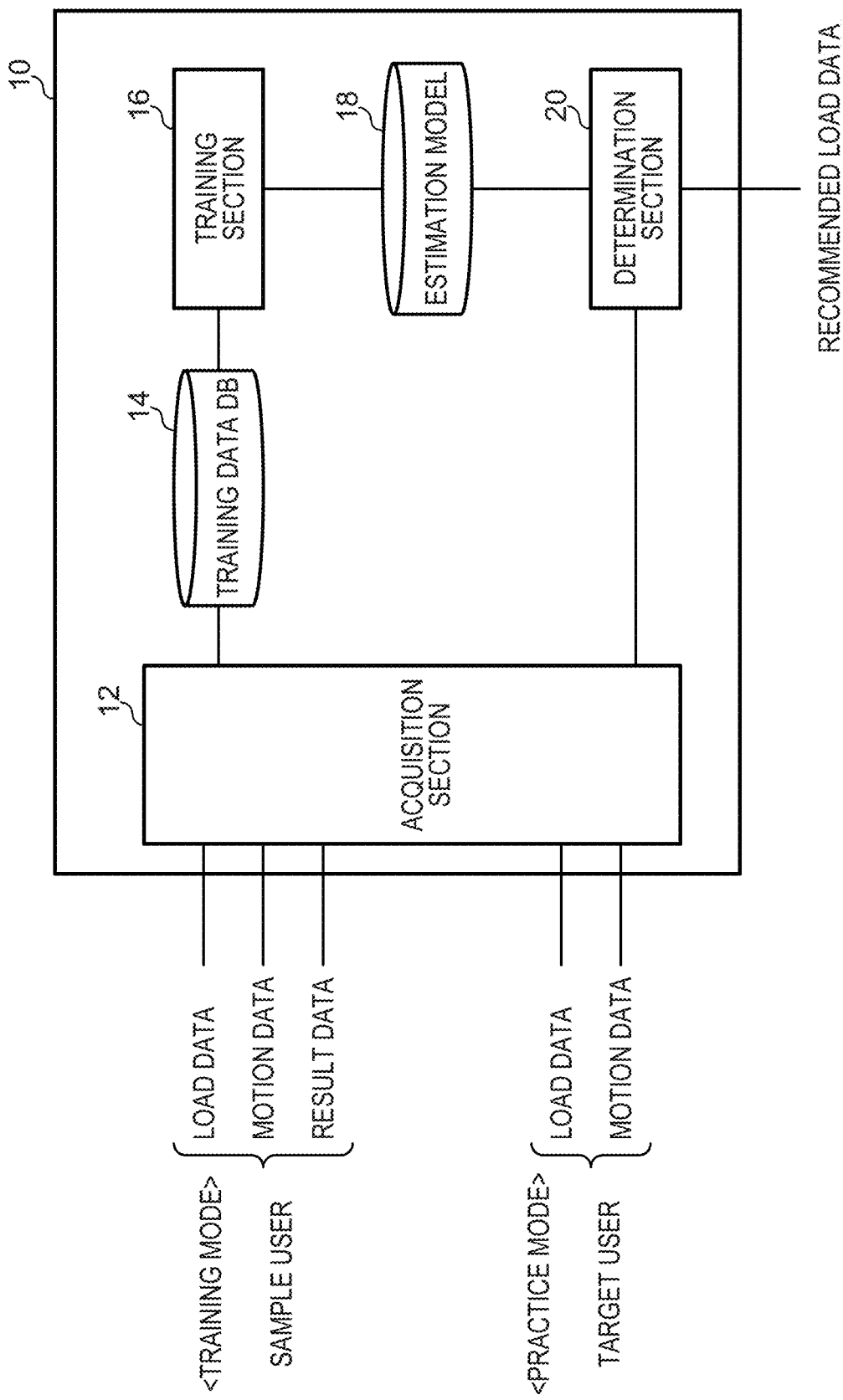
FIG. 1 is a functional block diagram of a recommended load determining device according to a first exemplary embodiment.

Description follows regarding an example of exemplary embodiments related to technology disclosed herein, with reference to the drawings. In each of the following exemplary embodiments description is of a recommended load determining device that determines a load to impart to a user in cases in which the user is performing a motion according to a prescribed motor task with a load imparted by a machine. The motor task is, for example, to improve a ball return rate in a table tennis rally, to improve a safe hit rate in baseball batting, to improve walking in rehabilitation, and the like. In such cases, a table tennis robot that returns and delivers table tennis balls, a batting machine, a treadmill, and the like are anticipated as load imparting devices, which are machines to impart a load to a user.

In each of the following exemplary embodiments, in cases in which there is data to define processing content of an estimation model itself, the expressions "input to the model" and "output from the model" indicate input to a functional means (model execution section) that is a computer or the like loaded with the model, and output from this same functional means. Cases in which an estimation model is itself data to define processing content are, for example, cases in which the estimation model itself is structure data and coupling weight data to define a neural network.

Note that the same reference numerals will be appended in the drawings to the same or equivalent configuration elements and portions. The dimensions and proportions in the drawings are also exaggerated for ease of explanation, and sometimes differ from actual proportions.

First Exemplary Embodiment

FIG. 1 is a block diagram illustrating a functional configuration of a recommended load determining device 10 according to a first exemplary embodiment. As illustrated in FIG. 1, the recommended load determining device 10 includes an acquisition section 12, a training data databased (DB) 14, a training section 16, an estimation model 18, and a determination section 20. The recommended load determining device 10 operates in two modes, these being a training mode to train the estimation model 18 and a practice mode to determine a recommended load by using the trained estimation model 18.

The acquisition section 12 acquires load data expressing a load imparted to a sample user in the training mode. The sample user is a user that executes a motor task to collect training data for training the estimation model 18. When a load imparting device is a table tennis robot or a pitching machine, the load data is, for example, a ball speed, spin, direction, and the like of a ball delivered or pitched from the load imparting device. The load data is, for example, a speed, inclination angle, or the like of a running belt in cases in which the load imparting device is a treadmill. The acquisition section 12 is able, for example, to acquire control information related to load such as motor torque from the load imparting device, and to acquire load data by measuring actual load imparted to a sample user.

Note that values defining loads to impart to a user sometimes include plural items, such as the "ball speed, spin, direction, etc." mentioned above. The acquisition section 12 may acquire a single item of load data from out of plural items, or may acquire load data of plural items therefrom, according to the item(s) changed when load is imparted, namely, according to the item(s) to be determined as the recommended load.

In the training mode the acquisition section 12 acquires motion data expressing motions of a single motion unit of a sample user under a load. The single motion unit is, for example, a motion indicating a swing in cases in which the motor task is batting in table tennis or baseball, and is a walking motion of a prescribed number of steps (for example, one step or two steps) when for performing walking practice. The motion data is, for example, displacement data of a particular location of a sample user or of an implement held when the sample user is performing the motion, muscle activity quantity data of a sample user, or differentiated data or integrated data thereof. The acquisition section 12 is able to acquire motion data by performing image analysis on images acquired using a camera of a sample user performing a motion, and by performing data processing on output values from a muscle potential sensor worn by the sample user.

In training mode the acquisition section 12 acquires result data accompanying motion of the sample user under a load. The result data is a ball return rate for a table tennis motor task, is a safe hit rate for a baseball batting motor task, and the like. The acquisition section 12 is able to acquire this result data by, for example, performing image analysis on images captured using a camera and by performing data processing on output values from various sensors. The acquisition section 12 may also acquire result data input manually in the training mode.

The acquisition section 12 stores the load data, motion data, and result data for each sample user acquired in the training mode in, for example, the training data DB 14 such as illustrated in FIG. 2. In the example of FIG. 2, "User No." is an identification number enabling sample users to be identified individually. "Attempt No." is a number indicating the data to be data of whichever number of attempt it is for each sample user, wherein one attempt is counted for each attempt at a motion of a single motion unit. The example of FIG. 2 illustrates an example in which load data, motion data, and result data is stored for 100 attempts for each sample user. "Capability Parameter" in FIG. 2 will be described later.

In practice mode the acquisition section 12 acquires load data expressing a load imparted to a target user who is the target for determining a recommended load, and acquires motion data expressing motion of a single motion unit of the target user under this load. Details regarding the load data and the motion data are similar to those of the load data and motion data acquired in the training mode described above. Note that in cases in which there is no discrimination made between the sample user and the target user in this description they will be simply referred to as "user".

The training section 16 is a functional section that functions in training mode. The training section 16 calculates a parameter related to a capability of each sample user at a motor task (hereafter also referred to as "capability parameter") based on load data and result data stored in the training data DB 14. The capability parameter can, for example, be load limit data expressing a value of a maximum load burden on a sample user from within a range of load values for one load item having an expectation of success, as indicated in result data for a motion, higher than a prescribed standard. The capability parameter may be a parameter expressing a relationship between load and a success expectation value for a motion. This parameter may be a parameter that identifies a graph expressing a relationship between a load value for a single load item and a success expectation value. The parameter may be a parameter to specify a heat map expressing a relationship between a load value for plural load items and a success expectation value. Reference here to "expectation of success" means a parameter expressing a value of a likelihood of success and may, for example, be a predicted success rate, or a predicted result value. An example of a result value is a magnitude of an error in landing position in an exemplary embodiment for table tennis described later. For the error in landing position, the expectation of success being higher as the predicted error gets smaller. Moreover, the "burden" for a user is a degree of difficulty for the user, with the expectation of success being smaller as the burden gets greater. For example, for an exemplary embodiment for table tennis, generally the higher the ball speed (load) of a ball delivered from a table tennis robot, the greater the burden, and the smaller the expectation of success.

The training section 16 stores the capability parameter calculated for each sample user in the "Capability Parameter" column of the training data DB 14. Each set of load data and motion data paired with a capability parameter is stored in the training data DB 14 as training data to train the estimation model 18. By learning correspondences of the load data and motion data, with respect to the capability parameter, the training section 16 generates the estimation model 18 for estimating and outputting a capability parameter of a target user, who is the target for recommended load determination, on being input with load data and motion data for the target user. The estimation model 18 is, for example, configured by a neural network or the like.

The determination section 20 is a functional section that functions in practice mode. The determination section 20 inputs load data and motion data for the target user as acquired by the acquisition section 12 into the estimation model 18. The determination section 20 determines recommended load data expressing a recommended load for the target user based on the capability parameter of the target user as output by the estimation model 18. Thus when load limit data is output from the estimation model 18 as the capability parameter as described above, the determination section 20 determines this load limit data as the recommended load data. Moreover, when a parameter expressing a relationship between a success expectation value with respect to a load and a motion is output as the capability parameter as described above, the determination section 20 determines the recommended load data based on the capability parameter.

For example, the determination section 20 is able to determine, as the recommended load data, load limit data expressing a value load at a maximum burden for the target user from out of a range of values of load for which an expectation of success is larger than the prescribed standard in a graph specified by the capability parameter. Moreover, the determination section 20 is able to determine, as the recommended load data, sets of load values for which the expectation of success is larger than the prescribed standard in a heat map specified by the capability parameter. The determination section 20 outputs the determined recommended load data. The output recommended load data may be utilized as control information to control a load imparting device, and may be presented to the target user and to an instructor of the target user or the like by being displayed on a display device.

Figure 3:
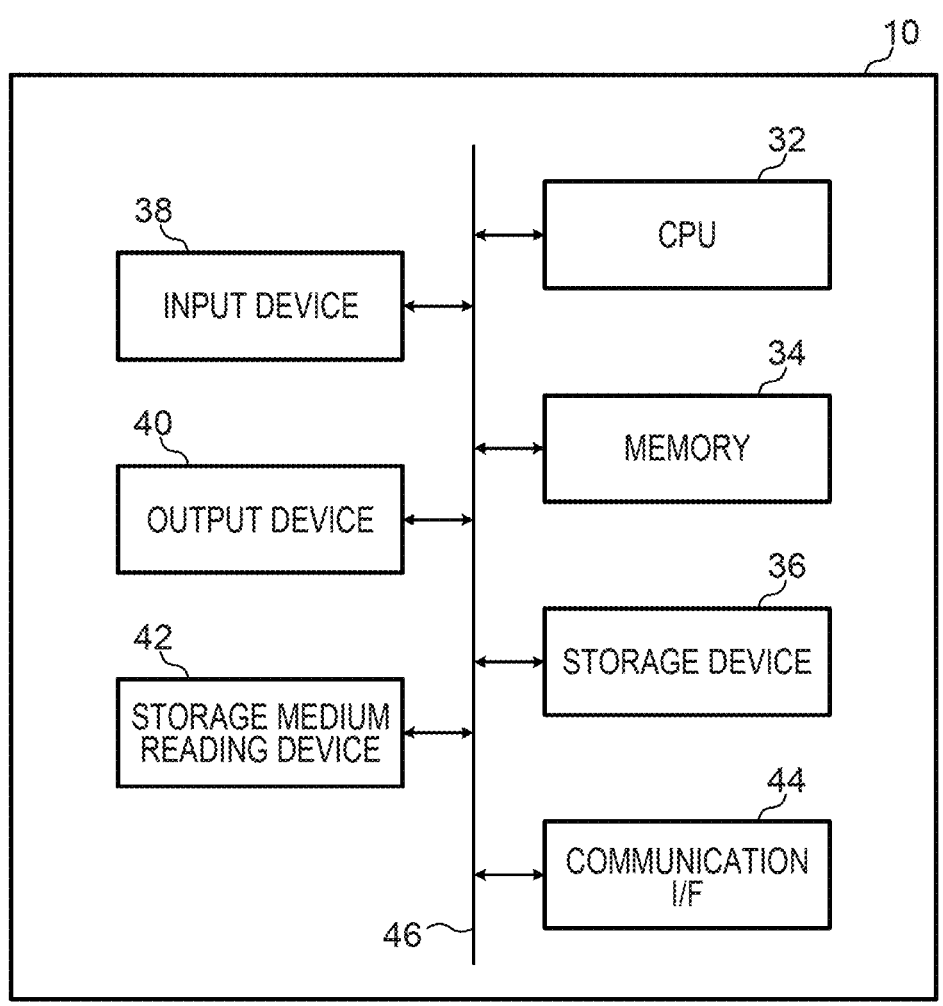
FIG. 3 is a block diagram illustrating a hardware configuration of a recommended load determining device.

FIG. 3 is a block diagram illustrating a hardware configuration of the recommended load determining device 10 according to a first exemplary embodiment. As illustrated in FIG. 3, the recommended load determining device 10 includes a central processing unit (CPU) 32, memory 34, a storage device 36, an input device 38, an output device 40, a storage medium reading device 42, and a communication interface (I/F) 44. These configurations are each connected together through a bus 46 so as to be capable of communicating with each other.

A recommended load determining program for executing both training mode processing and practice mode processing, as described later, is stored on the storage device 36. The CPU 32 is a central processing unit that executes various programs and controls each configuration. Namely, the CPU 32 reads a program from the storage device 36, and executes the program using the memory 34 as workspace. The CPU 32 controls each configuration and performs various computational processing according to the program stored in the storage device 36.

The memory 34 is configured by random access memory (RAM), and serves as a workspace to temporarily store programs and data. The storage device 36 is configured by a read only memory (ROM), and a hard disk drive (HDD), a solid state drive (SSD), or the like, and is stored with various programs including an operating system and various data.

The input device 38 is, for example, a device for performing various types of input, such as a keyboard, a mouse, or the like. The output device 40 is, for example, a device for outputting various types of information, such as a display, a printer, or the like. The output device 40 may also function as the input device 38 by using a touch panel display therefor. The storage medium reading device 42 performs reading of data stored on various types of storage medium, such as a compact disk read only memory (CD-ROM), digital versatile disc (DVD)-ROM, Blu-ray disc, universal serial bus (USB) memory, or the like, and writing of data to such storage media.

The communication I/F 44 is an interface for communication with other devices and, for example, employs a standard such as Ethernet (registered trademark), FDDI, Wi-Fi (registered trademark) or the like.

Next, description follows regarding operation of the recommended load determining device 10 according to the first exemplary embodiment.

Figure 4:
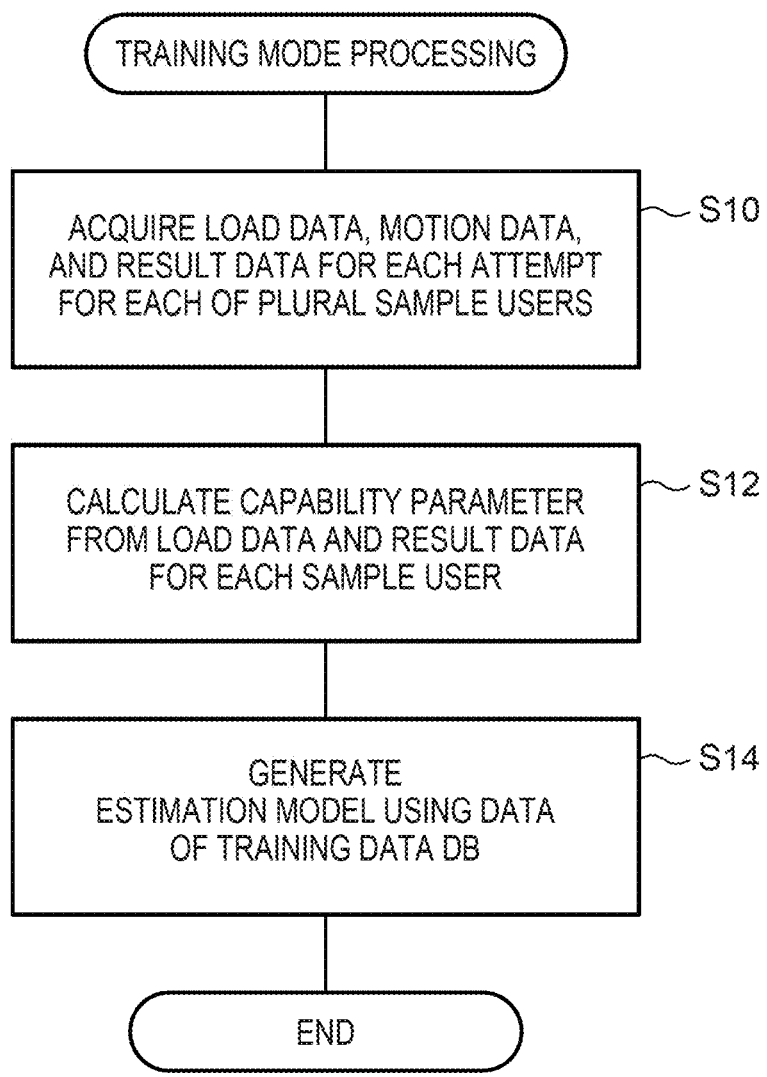
FIG. 4 is a flowchart illustrating an example of training mode processing of the first exemplary embodiment.

FIG. 4 is a flowchart illustrating a flow of training mode processing executed by the CPU 32 of the recommended load determining device 10. When the training mode is selected, the CPU 32 reads the recommended load determining program from the storage device 36, and the CPU 32 functions as each functional configuration of the recommended load determining device 10 by expanding and executing the recommended load determining program in the memory 34, so as to execute the training mode processing illustrated in FIG. 4.

At step S10 the acquisition section 12 acquires the load data, motion data, and result data for each attempt by the respective plural sample users, and stores this data in the training data DB 14.

Next at step S12, based on the data stored in the training data DB 14, the training section 16 calculates respective capability parameters from the load data and result data for each of the sample users, and stores these in the training data DB 14.

Next at step S14, the training section 16, by learning correspondences of the load data and motion data, with respect to the capability parameter, generates the estimation model 18 to output a capability parameter of a target user on being input with load data and motion data for the target user. The training section 16 stores the generated estimation model 18 in a prescribed storage area of the recommended load determining device 10, and then ends the training mode processing.

Figure 5:
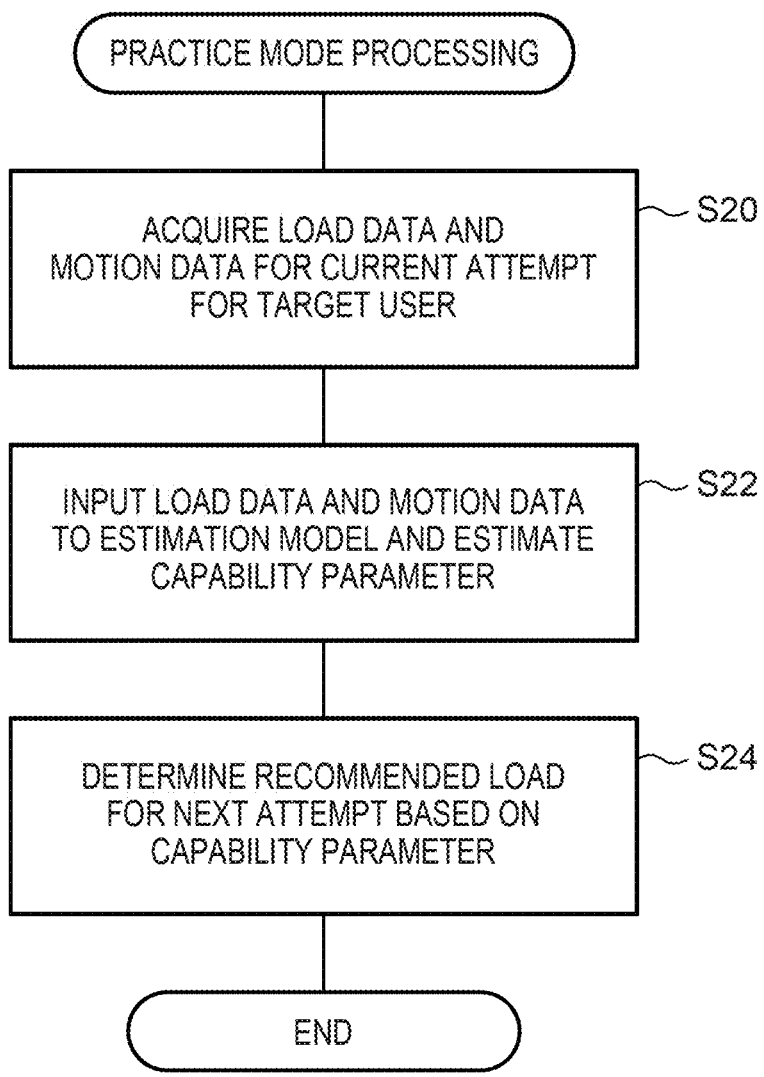
FIG. 5 is a flowchart illustrating an example of practice mode processing of the first exemplary embodiment.

FIG. 5 is a flowchart illustrating a flow of the practice mode processing executed by the CPU 32 of the recommended load determining device 10. When the practice mode has been selected, the CPU 32 reads the recommended load determining program from the storage device 36 and, by expanding and executing the recommended load determining program in the memory 34, the CPU 32 functions as each functional configuration of the recommended load determining device 10 such that the practice mode processing illustrated in FIG. 5 is executed. Note that the practice mode processing is an example of a recommended load determining method of the disclosure.

At step S20, the acquisition section 12 acquires the load data and motion data of the current attempt for the target user. Next at step S22, the determination section 20 inputs the load data and motion data for the target user as acquired by the acquisition section 12 into the estimation model 18, and estimates the capability parameter of the target user.

Next at step S24, based on the capability parameter of the target user as estimated and output by the estimation model 18, the determination section 20 determines and outputs recommended load data expressing a recommended load for the next attempt by the target user, and then ends the practice mode processing.

The recommended load is repeatedly determined by the practice mode processing being repeatedly executed for each attempt, enabling a succession of motor tasks to be executed by the target user.

As described above, the recommended load determining device according to the first exemplary embodiment acquires the load data expressing loads imparted to the target user, and the motion data expressing motions of a single motion unit of the target user under the respective loads. The recommended load determining device inputs the acquired load data and motion data into the estimation model for estimating and outputting a capability parameter of a target user on being input with load data and motion data, and thereby estimates the capability parameter of the target user. Based on the thereby estimated capability parameter of the target user, the recommended load determining device then determines the recommended load data expressing the recommended load for the target user. This thereby enables a load to be determined that is advantageous for skill improvement of the user when motor tasks imparting a load are being presented for execution by a user.

The following modifications may be made to the first exemplary embodiment. The recommended load determining device 10 according to the first exemplary embodiment is equipped with the training mode and the practice mode, however the recommended load determining device 10 may be equipped only with the practice mode, and not be equipped with the training mode. In such cases the recommended load determining device 10 does not include the training data DB 14 and the training section 16 required for training. The acquisition section 12 does not acquire the load data, the motion data, and the result data of the sample users.

The recommended load determining device 10 according to the first exemplary embodiment may lack the in-built training section 16, and may utilize an externally provided training function, such as by a server or the like on a network, through communication therewith. The in-built training data DB 14 may also be lacking, and data may be transmitted for recording in an externally provided training data DB.

The recommended load determining device 10 according to the first exemplary embodiment may be configured so as to acquire and utilize an external estimation model 18 that has already been trained. Moreover, an externally provided trained estimation model may be utilized by communication therewith.

These modifications of the first exemplary embodiment may also be applied in a similar manner to each of the exemplary embodiments from the second exemplary embodiment onward.

Second Exemplary Embodiment

Next, description follows regarding a second exemplary embodiment. The second exemplary embodiment is described for a cases in which the motor task is to improve a ball return rate in a table tennis rally, the load imparted to the user is the delivering or returning of a ball by a table tennis robot, and the motion of the user is a swing to return the ball hit by the table tennis robot.

Figure 6:
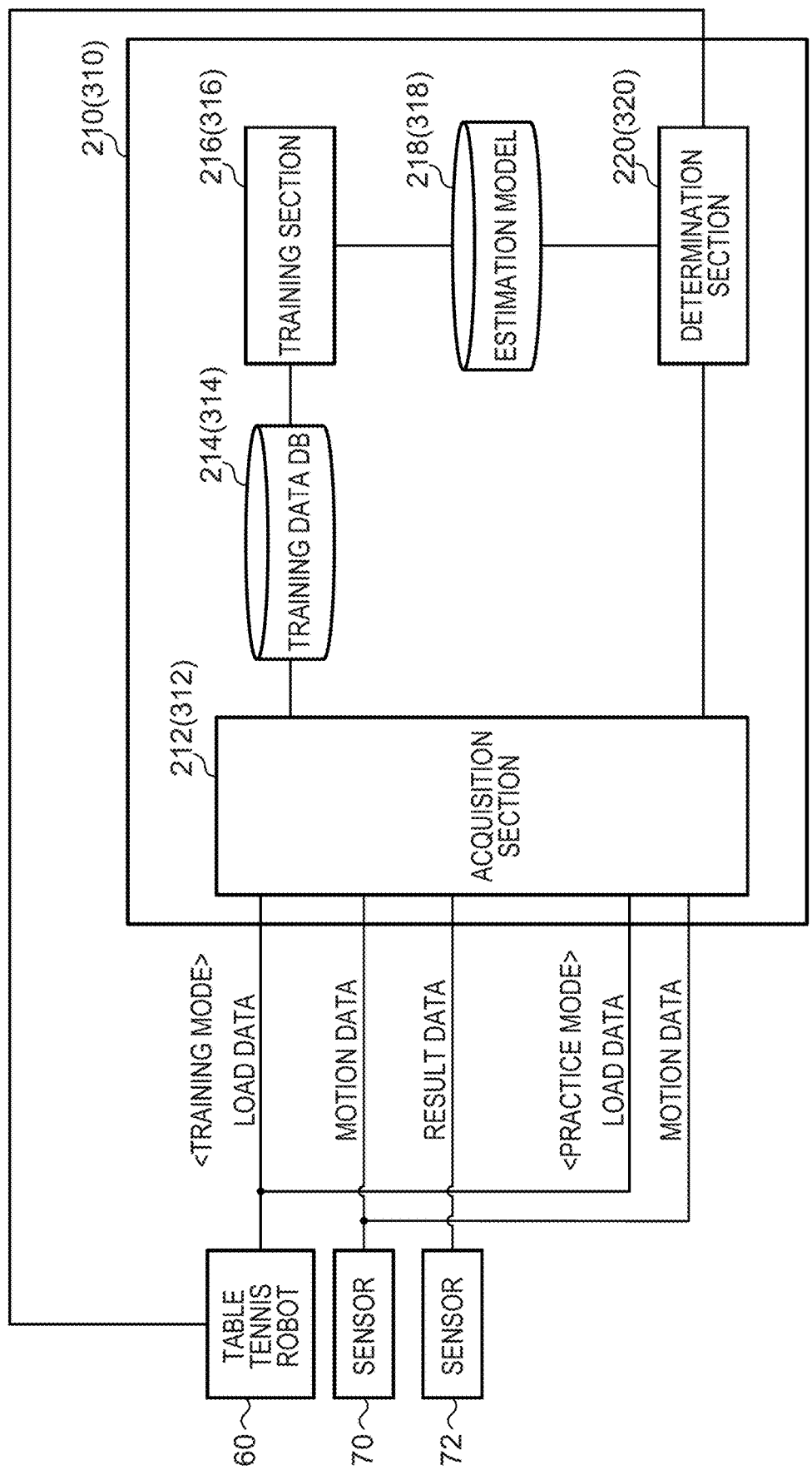
FIG. 6 is a functional block diagram of a recommended load determining device according to a second and third exemplary embodiment.

FIG. 6 is a block diagram illustrating a functional configuration of a recommended load determining device 210 according to the second exemplary embodiment. As illustrated in FIG. 6, a table tennis robot 60, a sensor 70, and a sensor 72 are each connected to the recommended load determining device 210.

Figure 7:
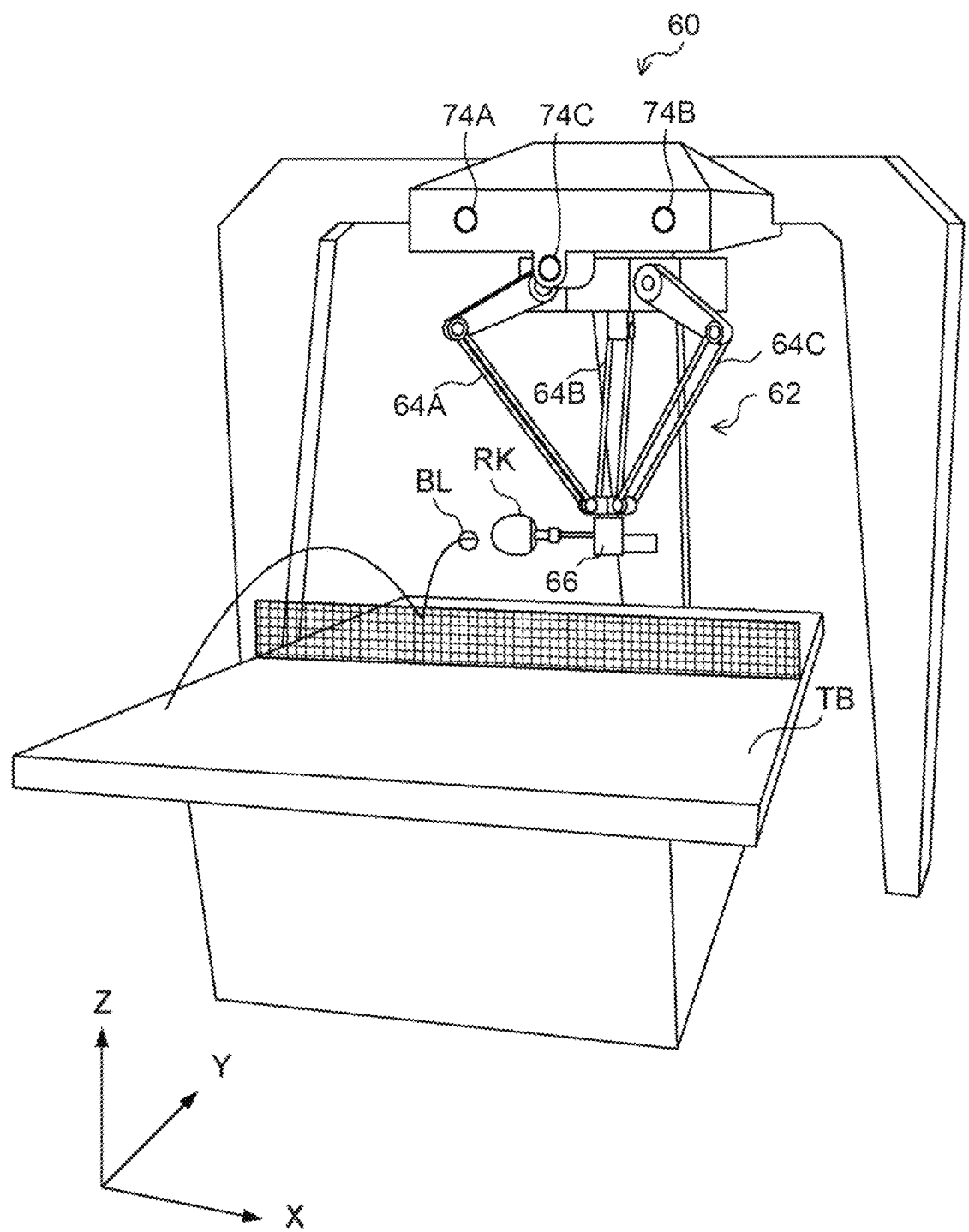
FIG. 7 is an external appearance diagram of a table tennis robot.

FIG. 7 illustrates an external appearance of the table tennis robot 60. The table tennis robot 60 is a robot that returns a table tennis ball BL hit by a non-illustrated user as it arrives after bouncing on a table tennis table TB, using a racket RK as a hitting implement. Note that because the focus of the present exemplary embodiment is on a load imparted to the user, namely on delivering or returning the ball BL with a particular load, detailed explanation regarding a function to recognize the ball returned by the user will be omitted.

As illustrated in FIG. 7, the table tennis robot 60 includes a moveable section 62 for supporting and moving the racket RK. In the example of FIG. 7, the moveable section 62 includes three robot arms 64A, 64B, 64C and a support section 66 for the racket RK. Namely, the moveable section 62 is a so-called parallel-link robot, and is a robot that controls the behavior of the racket RK supported by the support section 66 at the distal ends of the robot arms 64A, 64B, 64C by performing parallel control on the robot arms 64A, 64B, 64C. The support section 66 includes a drive mechanism for changing the orientation of the racket RK. Note that the moveable section 62 is not limited to being a parallel-link robot, and may be another type of robot. The table tennis robot 60 uses a non-illustrated control section to control the drive mechanism such that ball BL is returned with a hit speed as stipulated by control information. "Hit speed" is an example of load data.

Cameras 74A, 74B, 74C are installed to the table tennis robot 60. The cameras 74A, 74B are installed at positions enabling the user to be imaged from different angles, and perform image capture at a predetermined frame rate. The cameras 74A, 74B function as a so-called stereo camera. The sensor 70 configures, together with the cameras 74A, 74B, a non-illustrated image analysis section. The sensor 70 outputs information about the skeleton of the user by performing, for each frame, image analysis on the images captured by the cameras 74A, 74B. The skeleton information is time series data of three-dimensional positions (X, Y, Z) of each joint (joint 1 to joint n) of the user. Note that the joints included in the skeleton information are the joints needed to specify a swing motion and, for example, may be limited to the shoulder, elbow, and wrist of the dominant arm. There is no limitation to joints of the user, and a three-dimensional position of a center of a face of the racket RK held by the user or the like may also be included. "Skeleton information" is an example of motion data.

The camera 74C is installed at a position enabling the faces of the table tennis table TB to be imaged. The sensor 72 configures, together with the camera 74C, a non-illustrated image analysis section. The sensor 72 detects a landing position on the table tennis table TB of a ball returned by the user by performing image analysis on the images captured by the camera 74C, and computes and outputs an error (hereafter also referred to as "ball return error") between a pre-set position (for example, the center of the table tennis table TB) and the landing position. "Ball return error" is an example of result data.

As illustrated in FIG. 6, the recommended load determining device 210 includes, from a functional perspective, an acquisition section 212, a training data DB 214, a training section 216, an estimation model 218, and a determination section 220.

In training mode, the acquisition section 212 acquires, from the table tennis robot 60, a hit speed of a ball delivered (returned) by the table tennis robot 60 as load data indicating a load imparted to the sample user. For example, the acquisition section 212 is able to acquire the hit speed from control information set for controlling the drive mechanism of the table tennis robot 60 or from analysis results of images captured by the cameras 74A, 74B. The acquisition section 212 may also measure a speed of the ball delivered by the table tennis robot 60 using a non-illustrated sensor, and acquire the hit speed as indicated by a measurement value output from the sensor.

In training mode, the acquisition section 212 acquires the skeleton information of the sample user output by the sensor 70 as motion data of the sample user. Furthermore, in training mode the acquisition section 212 acquires the ball return error output from the sensor 72 as result data accompanying the motion of the sample user.

The acquisition section 212 stores the acquired hit speed, skeleton information, and ball return error in the training data DB 214. FIG. 8 illustrates an example of the training data DB 214. Items stored in the training data DB 214 are similar to those of the training data DB 14 in the first exemplary embodiment.

In practice mode, the acquisition section 212 acquires the hit speed that is the load data expressing the load imparted to the target user, and the skeleton information that is the motion data expressing the motion of the return swing of the target user in response to the hit ball. Details regarding methods to acquire the hit speed and the skeleton information are similar to those of the training mode described above. Note that the acquisition section 212 may acquire a hit speed indicating a recommended load determined in the determination section 220, described later, as the hit speed for the target user.

Figure 9:
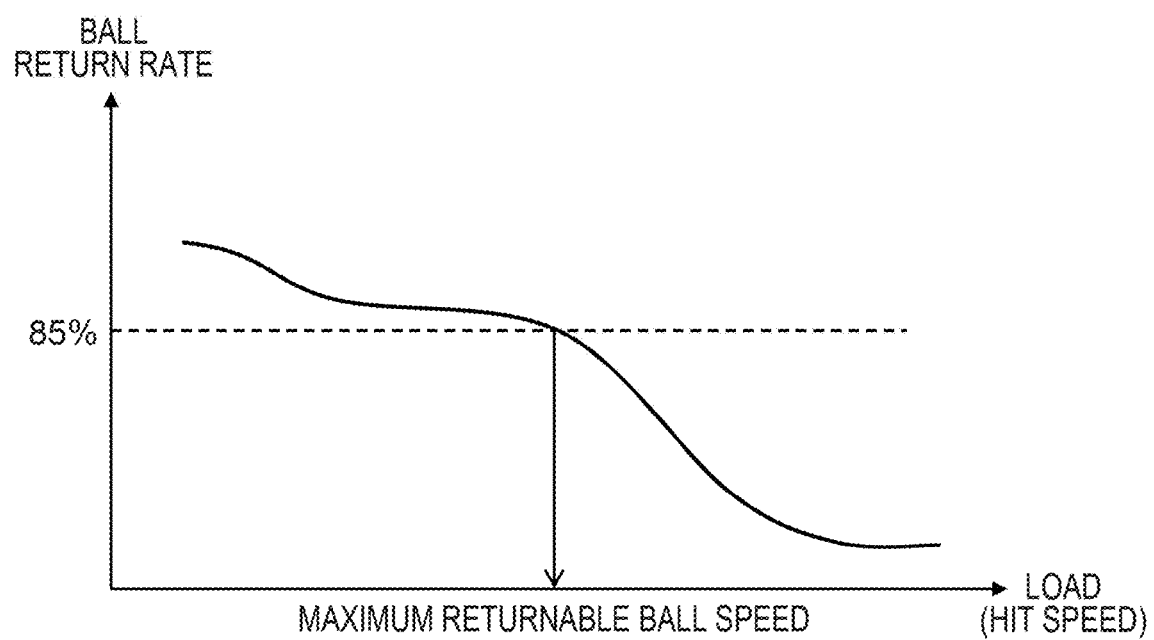
FIG. 9 is a graph illustrating a relationship between ball hit speed and ball return rate.

The training section 216 calculates a maximum returnable ball speed, which is an example of load limit data, as the capability parameter of each sample user. More specifically, from the training data of each sample user stored in the training data DB 214, the training section 216 calculates a ball return rate by the sample user at each hit speed. More specifically, the training section 216 takes success as being when the ball return error is a prescribed value (for example 75 cm) or less, and calculates the number of attempts when the ball was successfully returned as a proportion of the total number of attempts at a hit speed v±α (m/s) as the ball return rate for this hit speed v. For example, suppose that for a sample user of User No. 1, the number of attempts for which the hit speed was from 2.5 m/s to 3.5 m/s was 10 attempts, and from out of these the number of attempts when the ball was successfully returned was 5 attempts. In such cases the training section 216 calculates the ball return rate for the sample user of User No. 1 to be 50% at hit speed 3 m/s. The training section 216 calculates the ball return rate in a similar manner for each hit speed. Then as illustrated in FIG. 9, the training section 216 creates a graph expressing a relationship between hit speed and ball return rate, and from the graph finds the maximum hit speed for which the ball return rate is a prescribed value (for example, 85%) or lower as the maximum returnable ball speed. The training section 216 stores the maximum returnable ball speed found for each sample user in the training data DB 214, as illustrated in FIG. 8.

The training section 216 learns correspondences of the hit speeds and skeleton information for the sample users, with respect to the capability parameter therefor. The estimation model 218 is thereby generated to estimate and output a maximum returnable ball speed, which is the capability parameter of the target user, on being input with the hit speed and skeleton information for the target user.

The determination section 220 inputs the hit speed and skeleton information for the target user as acquired by the acquisition section 212 into the estimation model 218. The determination section 220 then determines the maximum returnable ball speed output by the estimation model 218 as the recommended load data for the target user, and outputs this to the table tennis robot 60. This accordingly means that recommended load data is set as control information in the table tennis robot 60, and control is performed at the next attempt so as to deliver (return) a ball at the hit speed indicated by this recommended load data.

A hardware configuration of the recommended load determining device 210 is, as illustrated in FIG. 3, similar to the hardware configuration of the recommended load determining device 10 according to the first exemplary embodiment, and so explanation thereof will be omitted. Note that a recommended load determining program for executing recommended load determination processing, described later, is stored in the storage device 36.

Next, description follows regarding operation of the recommended load determining device 210 according to the second exemplary embodiment.

Figure 10:
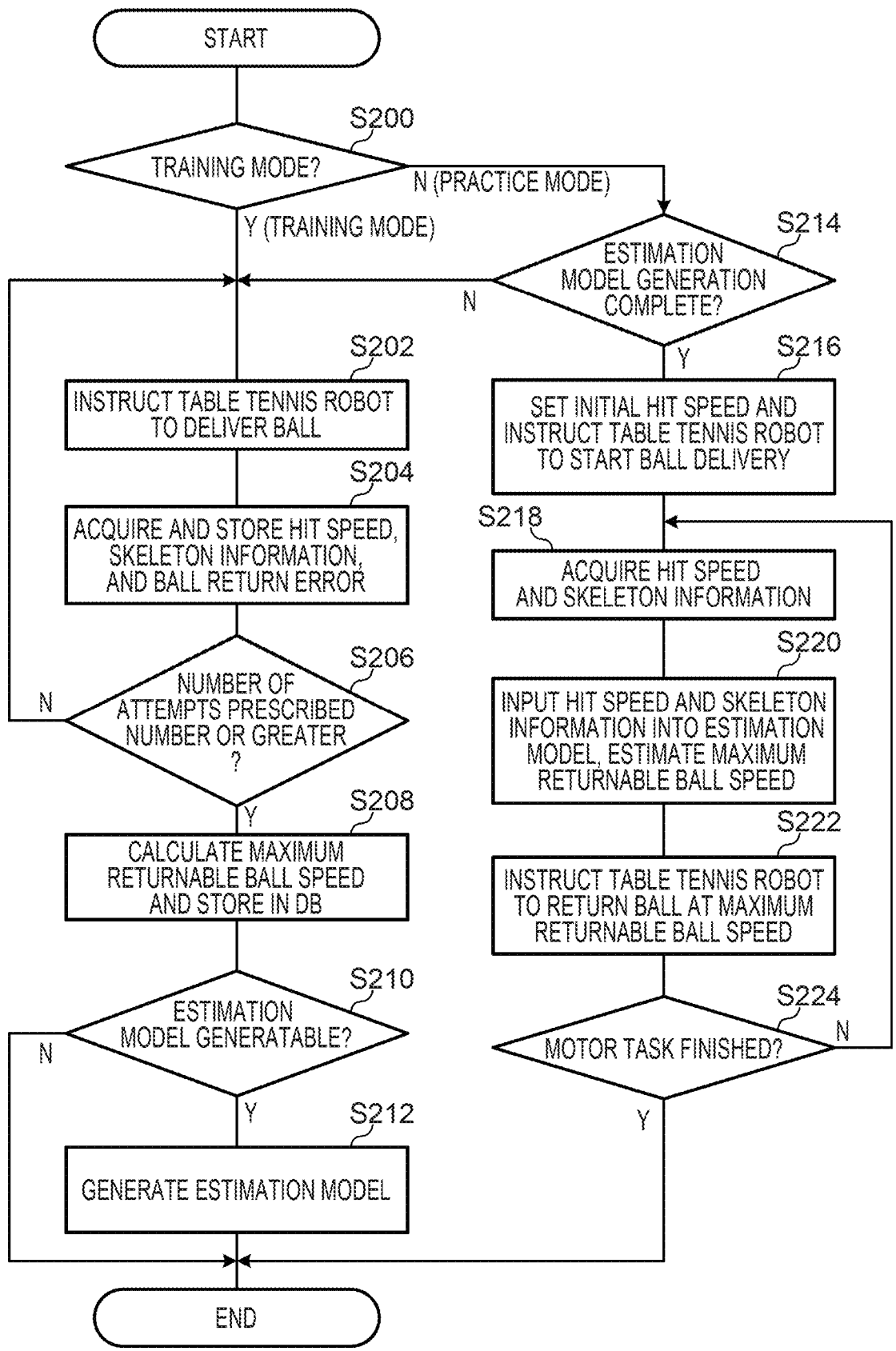
FIG. 10 is a flowchart illustrating an example of recommended load determination processing of the second exemplary embodiment.

FIG. 10 is a flowchart illustrating a flow of recommended load determination processing executed by the CPU 32 of the recommended load determining device 210. The CPU 32 reads the recommended load determining program from the storage device 36, and by expanding and executing the recommended load determining program in the memory 34, the CPU 32 functions as each functional configuration of the recommended load determining device 210 such that the recommended load determination processing illustrated in FIG. 10 is executed. Note that the recommended load determination processing is an example of a recommended load determining method of the disclosure.

At step S200, the acquisition section 212 determines whether or not the selected mode is the training mode. Processing transitions to step S202 when the training mode is selected, and processing transitions to step S214 when the practice mode is selected.

At step S202, the acquisition section 212 instructs the table tennis robot 60 to deliver (return) a ball. The hit speed of the ball delivered at this step may be set as control information for the table tennis robot 60 such that for the same sample user the hit speed is changed at each step, stepwise from an initial value.

Next at step S204, the acquisition section 212 acquires a hit speed of the ball delivered by instruction at step S202, and skeleton information representing a swing when the sample user returns this ball and ball return error thereof, and stores these in the training data DB 214.

Next at step S206, the acquisition section 212 determines whether or not the number of attempts for this sample user is a prescribed number of attempts (for example, 100 attempts) or greater. The prescribed number of attempts may be predetermined as a number of attempts needed as a number of items of training data for each sample user. Processing transitions to step S208 in cases in which the number of attempts is the prescribed number of attempts or greater, and processing returns to step S202 when less than the prescribed number of attempts.

At step S208, the training section 216 calculates the ball return rate for each hit speed from the training data of this sample user as stored in the training data DB 214. The training section 216 then finds a hit speed at which the ball return rate becomes the prescribed value (for example, 85%) or lower from a graph expressing a relationship between the hit speed and the ball return rate, and stores this as the maximum returnable ball speed in the training data DB 214.

Next at step S210, the training section 216 determines whether or not there is training data stored in the training data DB 214 for a number of sample users that is a number enabling generation of the estimation model 218. Processing transitions to step S212 when generation of the estimation model 218 is possible, and the recommended load determination processing is ended when the training data stored is not sufficient to generate the estimation model 218.

At step S212, the training section 216 generates the estimation model 218 by learning correspondences of the hit speeds and skeleton information for each sample user, with respect to the capability parameter thereof, and then ends the recommended load determination processing.

However, when the practice mode is selected and processing has transitioned to step S214, the determination section 220 determines whether or not generation of the estimation model 218 is complete. Processing transitions to step S216 when generation of the estimation model 218 is complete, and processing transitions to step S202 when generation is not complete.

At step S216, the acquisition section 212 sets the hit speed to the initial value and instructs the table tennis robot 60 to start delivering a ball. Next at step S218, the acquisition section 212 acquires a hit speed of the ball delivered by the table tennis robot 60 as instructed at step S216, and acquires skeleton information indicating the swing of the target user when returning the ball.

Next at step S220, the determination section 220 inputs the hit speed and the skeleton information for the target user acquired by the acquisition section 212 into the estimation model 218, and estimates the maximum returnable ball speed for the target user.

Next at step S222, the determination section 220 determines the maximum returnable ball speed estimated at step S220 as the recommended load data for the target user, and instructs the table tennis robot 60 to return the ball at the maximum returnable ball speed indicated by the recommended load data.

Next at step S224 the determination section 220 determines whether or not to end the motor task. For example, determination to end the motor task is made in cases in which there were no balls returned by the target user, and in cases in which a command indicating to end the motor task has been input, and the recommended load determination processing is ended. However, processing returns to step S218 when the motor task is not to be ended, and processing is repeated to acquire the hit speed of the ball delivered (returned) by the table tennis robot 60 under instruction at step S222 and the skeleton information indicating the swing of the target user when returning the ball.

As described above, in the recommended load determining device according to the second exemplary embodiment, for the motor task of improving the ball return rate using a table tennis robot, a load that is advantageous to skill improvement of the target user can be imparted due to delivering a ball that is the fastest within a returnable range for the target user.

Note that although the second exemplary embodiment has been described for an example in which the recommended load is determined for the motor task of improving the ball return rate using a table tennis robot, there is no limitation thereto. As in the examples given for the first exemplary embodiment, a motor task to improve the safe hit rate using a batting machine, and a motor task to improve walking in rehabilitation using a treadmill, may similarly be implemented as concrete exemplary embodiments of the second exemplary embodiment.

FIG. 11 illustrates an example of a training data DB 214A for a case in which the motor task is to improve the safe hit rate using a batting machine. In such cases a pitching speed of a ball delivered from the batting machine is acquired as the load data. Skeleton information indicating a swing when a user is batting the pitched ball is acquired as the motion data. A batting result (safe hit or easy fly) is acquired as the result data. Similarly to the graph illustrated in FIG. 9, a ball pitching speed at which a safe hit rate becomes a prescribed value (for example, 85%) or lower can be found from the relationship between ball pitching speed and safe hit rate as a maximum safe-hittable ball speed, and this employed as the capability parameter. An estimation model to estimate the fastest ball speed in a safe-hittable range for the target user as the recommended load data can be generated from the training data such as illustrated in FIG. 11.

FIG. 12 illustrates an example of a training data DB 214B for cases in which the motor task is to improve walking in rehabilitation using a treadmill. In this case a speed of a running belt of the treadmill is acquired as the load data. Skeleton information of the user walking on the running belt is acquired as the motion data. A variation in center of gravity in a single motion is, for example, acquired as result data based on the skeleton information. Note that the result data is not limited to being variation in center of gravity, and any index capable of evaluating a motion that enables walking without falling over may be employed therefor. Similarly to the graph illustrated in FIG. 9, a speed of the running belt such that the variation in center of gravity becomes a prescribed value or greater may be found as the maximum walkable speed from the relationship between the running belt speed and the variation in center of gravity, and this taken as the capability parameter. Note that the prescribed value may be a predetermined value such that there is a danger of falling over when the variation in center of gravity is this value or greater. An estimation model to estimate, as the recommended load data, the fastest running belt speed within a range the target user is able to walk at without falling over can be generated from the training data such as illustrated in FIG. 12.

Note that although the second exemplary embodiment has been described for a case in which the determined recommended load data is output to the table tennis robot, namely is for output to a load imparting device for controlling the load imparting device so as to impart a load to the target user, there is no limitation thereto. For example, data for displaying the latest recommended load data on a display device may be output to the display device at a prescribed time interval. For example, determined recommended load data may be displayed to an instructor who instructs the target user, such as a trainer, a physio therapist, or the like, such that control information relating to load may be set in a load imparting device as determined by the instructor.

Adopting such an approach enables safety of the target user to be considered, particularly in cases such as when the motor task is related to rehabilitation.

Moreover, although in the second exemplary embodiment a case is described in which the maximum returnable ball speed, which is an example of the load limit data, is estimated as the capability parameter, there is no limitation thereto. For example, a parameter to specify a graph such as illustrated in FIG. 9 may be estimated as the capability parameter, so as to determine the recommended load data based on this graph. For example, recommended load data may be determined at random from loads contained in a prescribed range of ball return rates (for example, from 80% to 85%). Alternatively, a statistical value such as an average, median, or mode of the loads contained in the prescribed range of ball return rates may be determined as the recommended load data.

Third Exemplary Embodiment

Next description follows regarding a third exemplary embodiment. The third exemplary embodiment will be described for a case in which, similarly to the second exemplary embodiment, the motor task is to improve a ball return rate in a table tennis rally, the load imparted to the user is a return ball from a table tennis robot, and a motion of the user is a swing to return the ball hit by the table tennis robot.

As illustrated in FIG. 6, a recommended load determining device 310 according to the third exemplary embodiment includes, from a functional perspective, an acquisition section 312, a training data DB 314, a training section 316, an estimation model 318, and a determination section 320.

Similarly to the acquisition section 212 of the second exemplary embodiment, in training mode the acquisition section 312 acquires load data, motion data, and result data, and in practice mode acquires load data and motion data. The motion data is skeleton information of the user similar to that of the second exemplary embodiment, and the result data is ball return error similar to that of the second exemplary embodiment.

In the third exemplary embodiment the load is made multi-dimensional, and the acquisition section 312 acquires plural items of load data. For example, the acquisition section 312 also acquires a ball spin, indicating a rotation speed of a ball, and a relative position thereof as the plural items of load data, in addition to the hit speed similar to in the second exemplary embodiment. The relative position is a relative position of a landing position of a ball BL returned by the table tennis robot 60 on the table tennis table TB, relative to a position of the user. The acquisition section 312 is able to acquire such load data from control information set in the table tennis robot 60. Moreover, the load data may be acquired by detecting a landing position of the ball BL and the position of the user, the ball spin, and the like using non-illustrated sensors.

The acquisition section 312 stores the acquired hit speed, ball spin, relative position, skeleton information, and ball return error in the training data DB 314. FIG. 13 illustrates an example of the training data DB 314. Items in the training data DB 314 are similar to those of the training data DB 214 of the second exemplary embodiment, except in that there are plural items of load data.

The training section 316 calculates, as a capability parameter for each sample user, a heat map indicating relationships between a load value for each of the plural items of load data, and the ball return rate when the load indicated by this load data is imparted. More specifically, the training section 316 allocates the load data values across plural steps. For example, hit speeds of 2.5 m/s to 3.5 m/s are treated as 3 m/s. The training section 316 calculates the ball return rate similarly to in the second exemplary embodiment for each allocated set of values for hit speed, ball spin, and relative position. For a heat map having an axis for each of hit speed, ball spin, and relative position, the training section 316 derives the heat map by storing the calculated ball return rate in cells corresponding to each of the load data value sets, and stores this heat map in the "Capability Parameter" row of the training data DB 314, as illustrated in FIG. 13. Note that in the example illustrated in FIG. 13, the ball return rate of the heat map is expressed by darkness/lightness.

Figure 14:
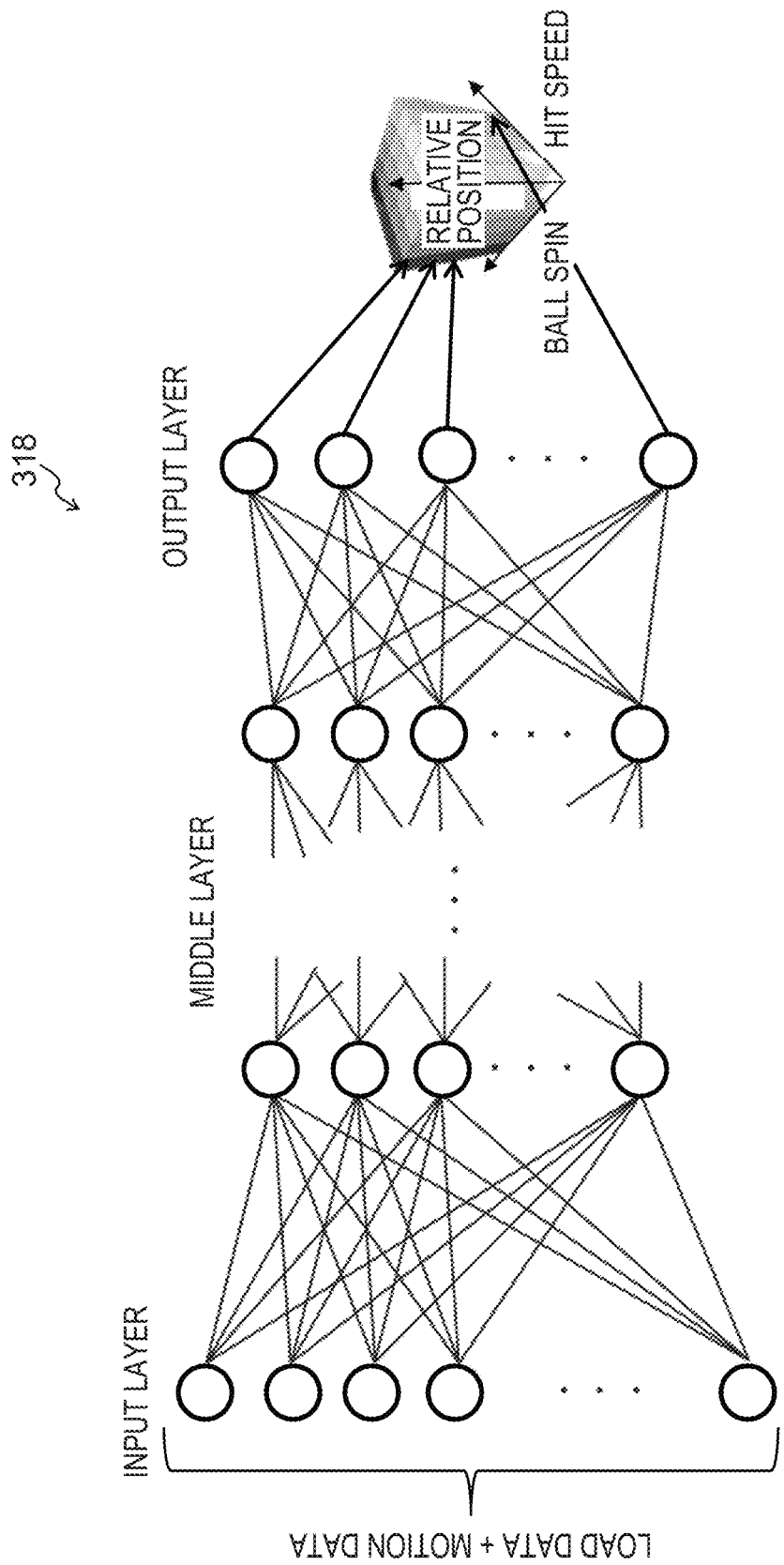
FIG. 14 is a diagram illustrating an example of an estimation model of the third exemplary embodiment.

The training section 316 learns correspondences of the plural items of load data (hit speed, ball spin, relative position) and the skeleton information for the sample user, with respect to the capability parameter thereof. The training section 316 accordingly generates the estimation model 318 to estimate and output a heat map, which is the capability parameter for the target user, on being input with the plural load data and the skeleton information for the target user. The estimation model 318 may, for example, be implemented by a neural network such as illustrated in FIG. 14. In such cases, an input to each neuron of the input layer corresponds to each element of multi-dimensional data resulting from combining the plural items of load data with the skeleton information, and the output from each neuron of the output layer corresponds to the values of each cell of the heat map.

The determination section 320 estimates the heat map for the target user by inputting the plural items of load data (hit speed, ball spin, relative position) and the skeleton information for the target user, as acquired by the acquisition section 312, into the estimation model 318. The determination section 320 determines the recommended load data for the next attempt based on the estimated heat map. Moreover, the determination section 320 may output data to display a visualization of the estimated heat map.

Figure 15:
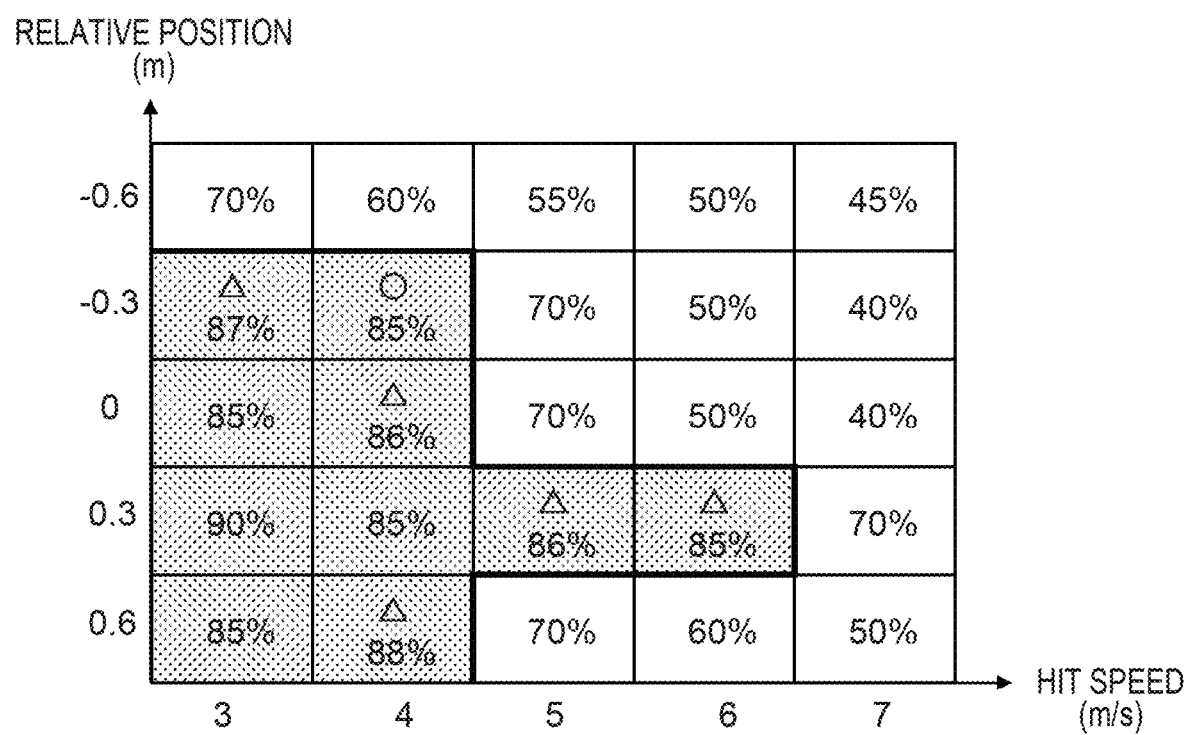
FIG. 15 is a diagram to explain determining recommended load data based on a heat map.

Description follows regarding a method of determining the recommended load data, with reference to the heat map illustrated in FIG. 15. Note that for ease of explanation, in FIG. 15 a two dimensional heat map is employed for two items of load data (hit speed and relative position) is described. Similar applies to FIG. 18 to FIG. 21, FIG. 28, and FIG. 29. The determination section 320 identifies cells in the heat map for which the ball return rate is a prescribed value (for example, 85%) or higher (the shaded cells in FIG. 15). The determination section 320 determines the recommended load data from a combination of load data values contained within the range indicated by the identified cells.

For example, the determination section 320 may select a cell having the minimum ball return rate from out of the identified cells, and determine the recommended load data from the combination of load data values contained in the range indicated by this cell. For example, the determination section 320 may select the cell indicated by a circle mark in FIG. 15, and determine the recommended load data to be a hit speed of 4 m/s and a relative position of −0.3 m. Note that due to the values of the load data corresponding to each cell being values having a spread, it may be predetermined so as to select a median, maximum value, or minimum value from within this spread. Moreover, it may be determined so as to determine a value at random in a range from the minimum value to the maximum value therein.

From the objective of skill improvement of the target user, the recommended load data may be determined so as to impart a more severe load. More specifically, the determination section 320 may determine the recommended load data from values of a range indicated by cells in the heat map having a ball return rate of the prescribed value or higher that are cells adjacent to cells for which the ball return rate is less than a prescribed value (the cells indicated by the circular mark or the triangular mark in FIG. 15). More precisely, the determination section 320 may determine the recommended load data from values above a boundary (the bold line in FIG. 15) in the heat map between cells having a ball return rate of the prescribed value or higher, and the cells having a ball return rate of less than the prescribed value. The determination section 320 outputs the determined load data to the table tennis robot 60. Recommended load data is accordingly set as control information in the table tennis robot 60, and at the next attempt control is performed such that a ball is delivered (returned) with the hit speed, ball spin, and relative position as indicated by this recommended load data.

A hardware configuration of the recommended load determining device 310 is similar to the hardware configuration of the recommended load determining device 10 according to the first exemplary embodiment as illustrated in FIG. 3, and so explanation thereof will be omitted. Note that a recommended load determining program for executing recommended load determination processing, described later, is stored in the storage device 36.

Next, description follows regarding operation of the recommended load determining device 310 according to the third exemplary embodiment.

Figure 16:
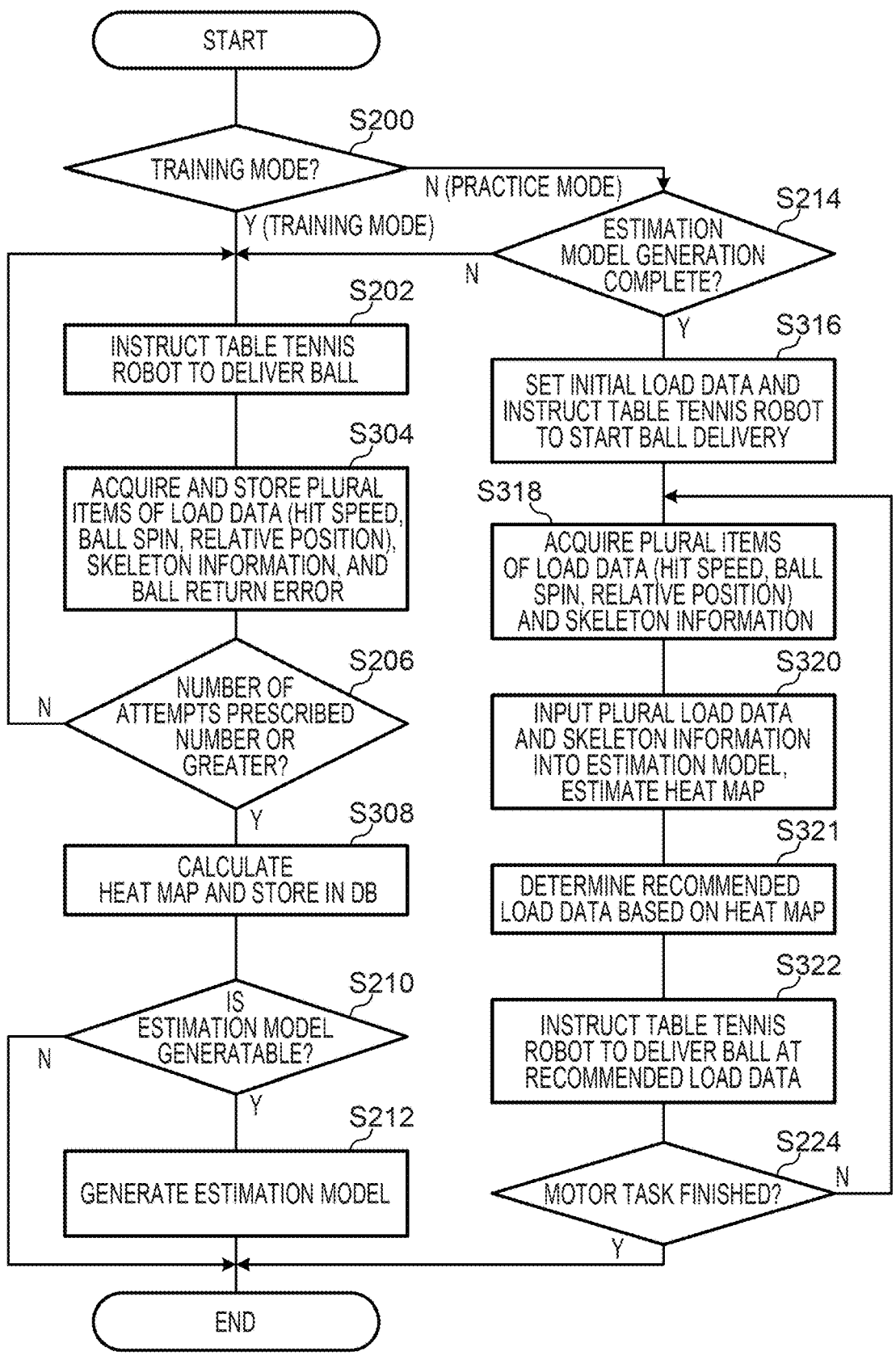
FIG. 16 is a flowchart illustrating an example of a recommended load determination processing of the third exemplary embodiment.

FIG. 16 is a flowchart illustrating a flow of recommended load determination processing executed by the CPU 32 of the recommended load determining device 310. The CPU 32 reads a recommended load determining program from the storage device 36, and by expanding and executing the recommended load determining program in the memory 34, the CPU 32 functions as each functional configuration of the recommended load determining device 310 such that the recommended load determination processing illustrated in FIG. 16 is executed. Note that the same step numbers are appended in the recommended load determination processing of the third exemplary embodiment to processing similar to the recommended load determination processing of the second exemplary embodiment (FIG. 10), and detailed explanation thereof will be omitted.

When affirmative determination is made at step S200, and processing has transitioned to step S202 onward in the training mode, processing of a step S304 is executed instead of step S204 of the recommended load determination processing of the second exemplary embodiment. At step S304, the acquisition section 312 acquires plural items of load data (hit speed, ball spin, relative position), skeleton information, and ball return error, and stores these in the training data DB 314.

Moreover, processing of step S308 is executed instead of step S208 of the recommended load determination processing of the second exemplary embodiment. At step S308, the training section 316 calculates as a capability parameter for each sample user a heat map indicating a relationship between a value of a load for each of plural items of load data with respect to the ball return rate when imparted with the load indicated by this load data.

However, when negative determination is made at step S200 and processing has transitioned to step S214 onward in the practice mode, processing transitions to step S316 when determined at step S214 that generation of the estimation model 318 is complete.

At step S316, the acquisition section 312 instructs the table tennis robot 60 to set each of the hit speed, ball spin, and relative position to initial values thereof and to start delivering a ball. Next at step S318, the acquisition section 312 acquires the hit speed, ball spin, and relative position of the ball delivered by the table tennis robot 60 as instructed at step S316, and acquires the skeleton information indicating the swing when the target user is returning a ball in response to the hit ball.

Next at step S320, the determination section 320 inputs the plural items of load data (hit speed, ball spin, and relative position) and the skeleton information for the target user as acquired by the acquisition section 312 into the estimation model 318, and estimates a heat map for the target user. Next at step S321, the determination section 320 determines the recommended load data for the next attempt based on the estimated heat map.

Next at step S322, the determination section 320 instructs the table tennis robot 60 to return with the hit speed, ball spin, and relative position indicated by the recommended load data determined at step S321.

As described above, in the recommended load determining device according to the third exemplary embodiment, for the motor task of improving the ball return rate using a table tennis robot, a load that combines plural items within a ball returnable range for the target user can be imparted to the target user. Moreover, a load that is advantageous to skill improvement of the target user can be imparted by selecting a load with the greatest burden for the user from out of the ball returnable range.

Fourth Exemplary Embodiment

Next, description follows regarding a fourth exemplary embodiment. Similarly to in the third exemplary embodiment, the fourth exemplary embodiment will be described for a case in which the motor task is to improve a ball return rate in a table tennis rally, the load imparted to the user is a return ball from a table tennis robot, and a motion of the user is a swing to return the ball hit by the table tennis robot. As described with reference to FIG. 15, in the third exemplary embodiment a case was described in which a range of load data for which the ball return rate is the prescribed value or higher is identified, and the recommended load data values are determined from this range. The recommended load data for the next attempt are a single set of values for the plural items of load data, however there are plural load value sets contained in the identified range as candidates for the recommended load data.

In the fourth exemplary embodiment a method will be described for narrowing down the recommended load data to be determined from the identified range so as to enable determination of more advantageous recommended load data.

Figure 17:
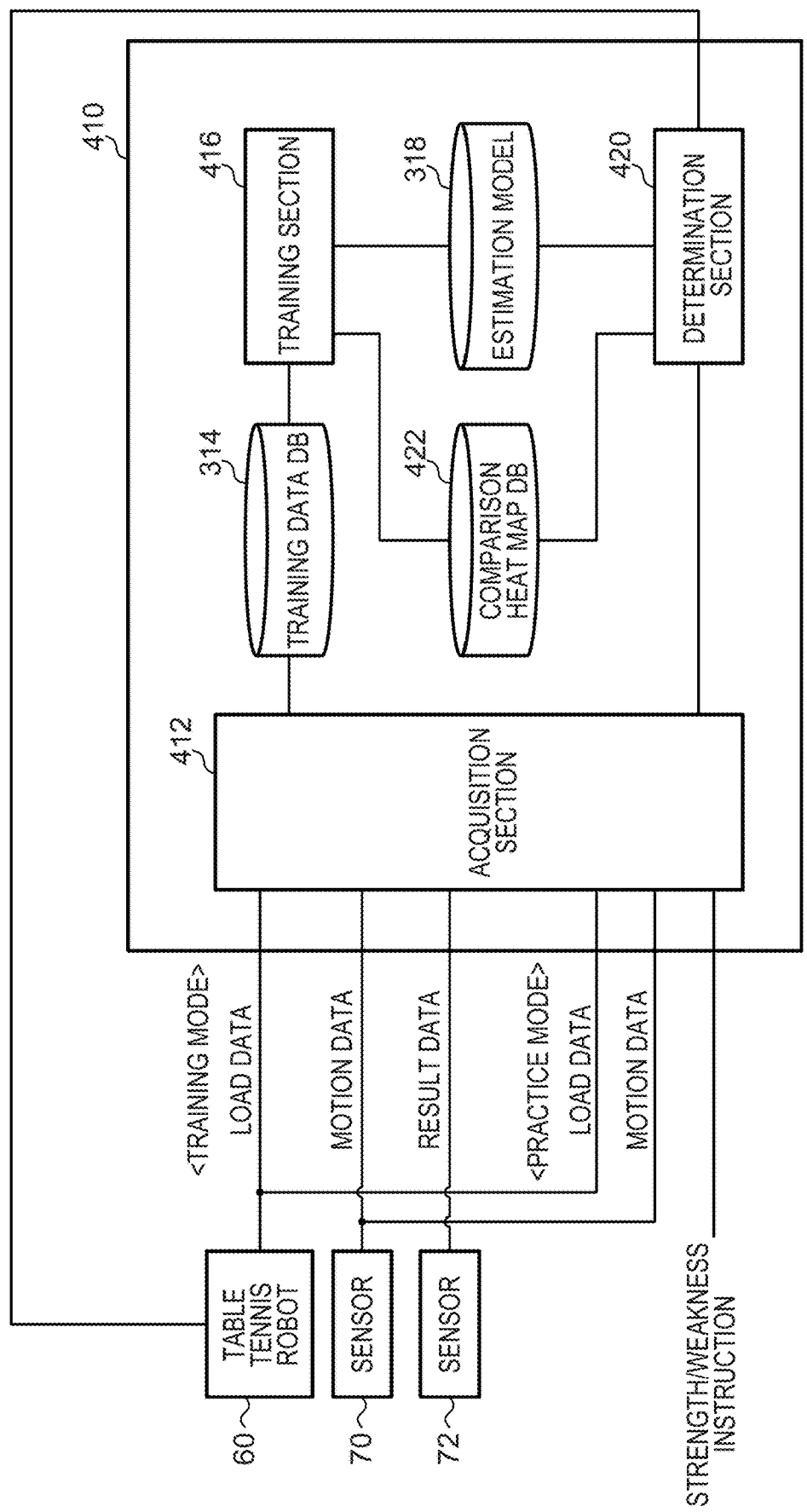
FIG. 17 is a functional block diagram of a recommended load determining device according to a fourth exemplary embodiment.

As illustrated in FIG. 17, a recommended load determining device 410 according to the fourth exemplary embodiment includes, from a functional perspective, an acquisition section 412, a training data DB 314, a training section 416, a comparison heat map DB 422, an estimation model 318, and a determination section 420.

Similarly to the acquisition section 312 according to the third exemplary embodiment, in training mode the acquisition section 412 acquires plural items of load data, motion data, and result data, and in practice mode acquires plural items of load data and motion data. For example, the plural items of load data are hit speed, ball spin, and relative position, the motion data is skeleton information of the user, and the result data is ball return error. Furthermore, in the practice mode the acquisition section 412 acquires a strength/weakness instruction indicating whether the target user wants to practice a strength or wants to practice a weakness. This instruction is input to the recommended load determining device 410 through the input device 38.

Similarly to the training section 316 of the third exemplary embodiment, the training section 416 calculates a heat map as a capability parameter for each sample user, and generates the estimation model 318. Furthermore, the training section 416 also creates a comparison heat map to identify a relative strength range indicating a range of load for which the target user is relatively strong compared to other users, and a relative weakness range indicating a range of load for which the target user is relatively weak. A strength is when the target user has a higher expectation of success that other users, and a weakness is when the target user has a smaller expectation of success that other users.

Figure 18:
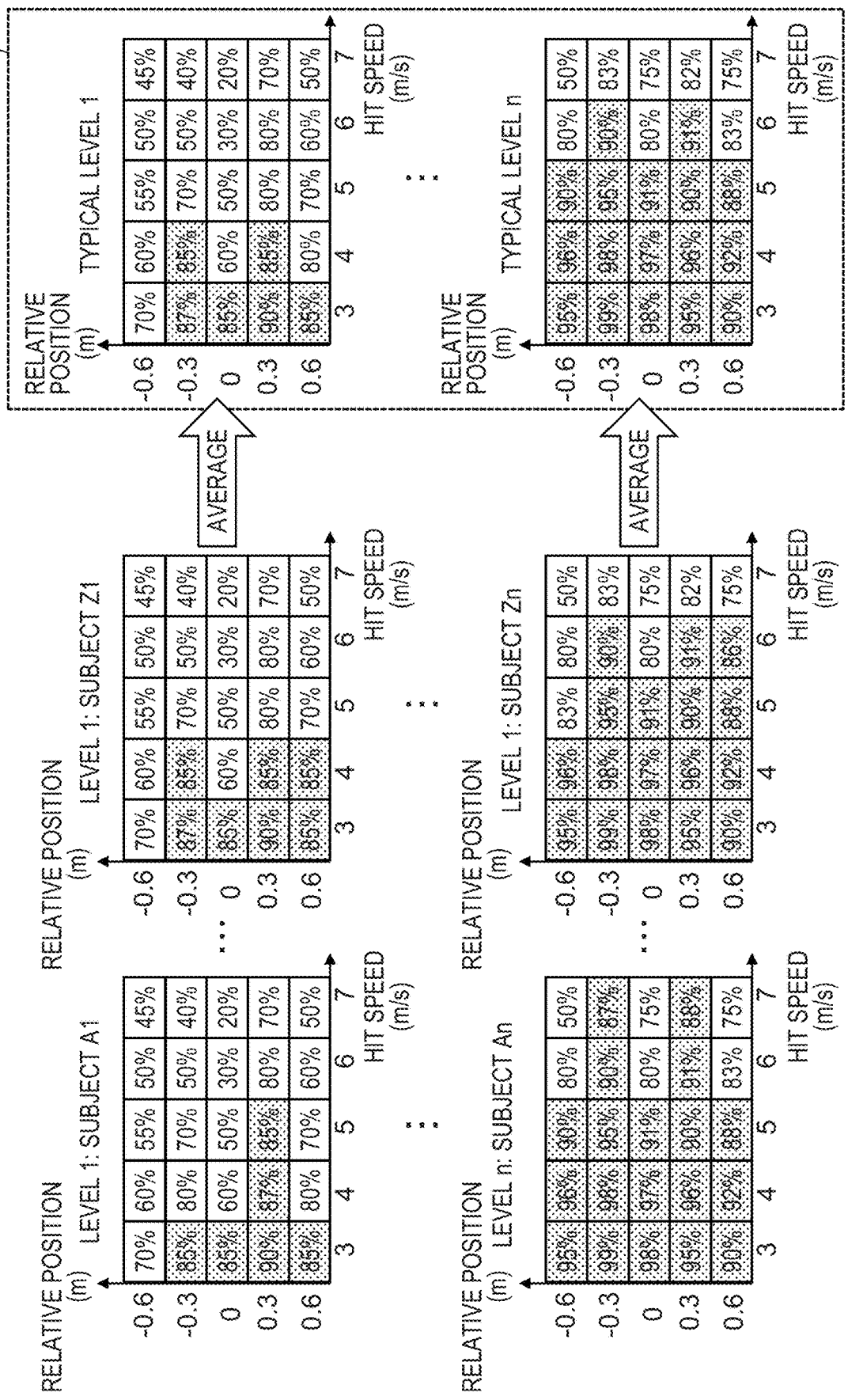
FIG. 18 is a diagram to explain a comparative heat map.

More specifically, the training section 416 separates the sample users having training data stored in the training data DB 314 by level according to capability for the motor task. This separation by level may be performed manually, and may be performed using the capability parameters calculated in the process by which the training section 416 generates the estimation model 318. For example, the training section 416 determines a level of each sample user based on level steps defined according to a proportion in a heat map of the number of cells having a ball return rate of a prescribed value (for example, 85%) or higher with respect to the total number of cells. The number of level steps may be appropriately set according to the number of sample users or the like. As illustrated in FIG. 18, the training section 416 calculates a heat map typical for each level from the heat maps calculated for respective sample users of the same level. For example, the training section 416 calculates a statistical value, such as an average, median, or mode of the values for each cell of the heat maps for respective sample users of the same level as a value for each cell in the typical heat map. The training section 416 then stores the typical heat map calculated for each level as a comparison heat map in the comparison heat map DB 422.

The determination section 420 estimates the heat map of the target user using the estimation model 318 similarly to the determination section 320 of the third exemplary embodiment. The determination section 420 then compares the heat map of the target user against the comparison heat map, and creates a relative strength/weakness map to identify the relative strength range and the relative weakness range of the target user. The determination section 420 determines a set of load values in the relative strength range or in the relative weakness range of the thus created relative strength/weakness map as the recommended load data.

More specifically, based on the heat map of the target user, the determination section 420 determines a level of the target user, and identifies the typical heat map of the same level as the target user, or of a level one rank higher, as the comparison heat map, then acquires this from the comparison heat map DB 422. Note that a reason for employing the level one rank higher is to consider skill improvement. The determination section 420 prepares an empty relative strength/weakness map including cells corresponding to each cell of a heat map. The determination section 420 creates the relative strength/weakness map by placing in each cell of the empty relative strength/weakness map information corresponding to results of a comparison of each cell value (ball return rate) between the target user heat map and the comparison heat map.

Figure 19:
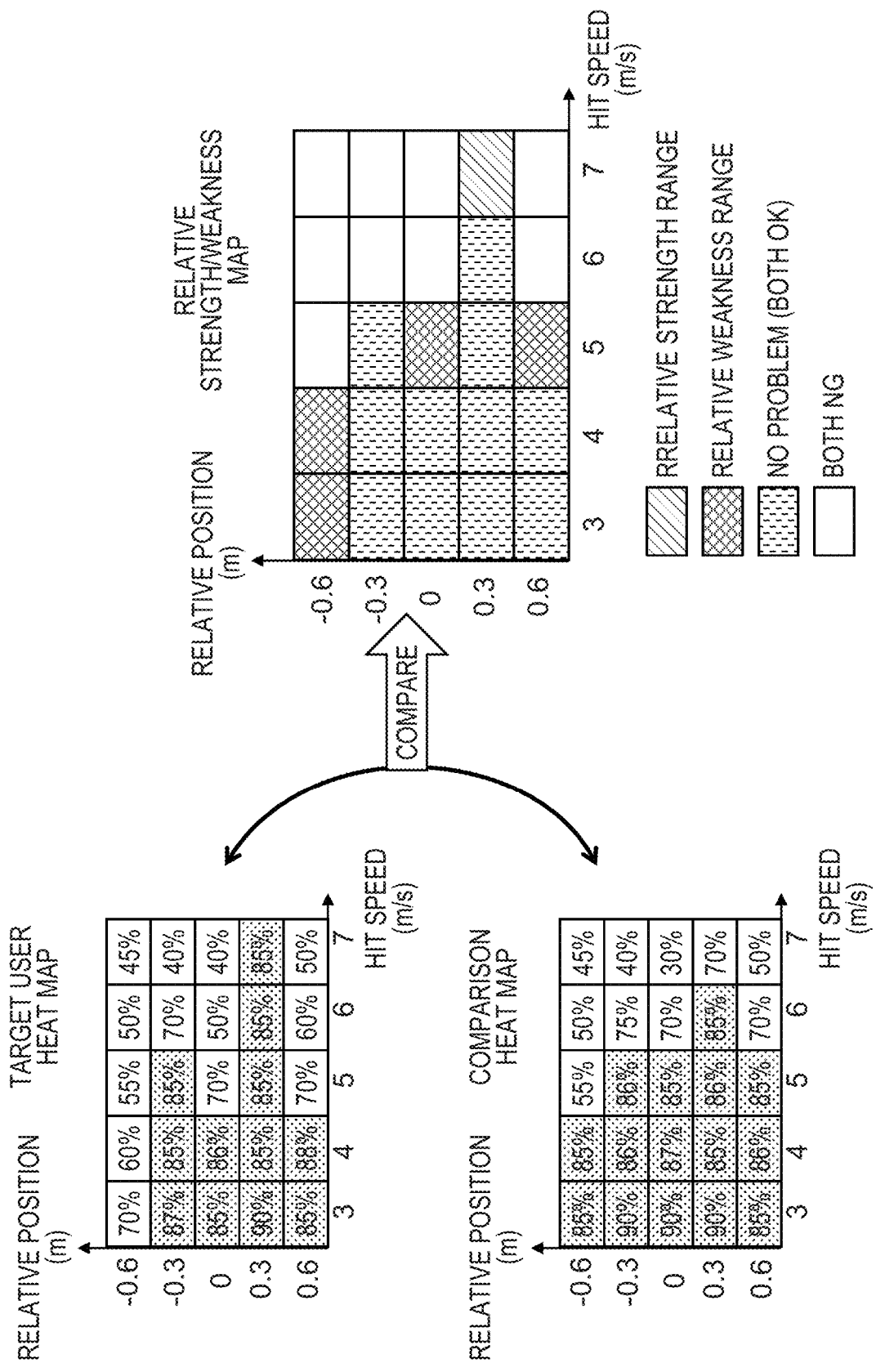
FIG. 19 is a diagram to explain a relative strength/weakness map.

More specifically, as illustrated in FIG. 19, the determination section 420 identifies as the relative strength range any cells that have a ball return rate in the target user heat map of the prescribed value (for example, 85%) or higher and that have a ball return rate in the comparison heat map of less than the prescribed value. The determination section 420 also identifies as the relative weaknesses range any cells that have a ball return rate in the target user heat map of less than the prescribed value and that have a ball return rate in the comparison heat map of the prescribed value or higher. Note that in the example of FIG. 19 the cells having a ball return rate of the prescribed value or higher in both the target user heat map and the comparison heat map are identified as a no-problem range. Moreover, the cells having a ball return rate of less than the prescribed value in both the target user heat map and the comparison heat map are identified as a both-NG range.

In cases in which "strength" is instructed as the strength/weakness instruction acquired by the acquisition section 412, the determination section 420 determines the recommended load data based on the relative strength range of the relative strength/weakness map. In cases in which "weakness" is instructed as the strength/weakness instruction acquired by the acquisition section 412, the determination section 420 determines the recommended load data based on the relative weakness range of the relative strength/weakness map. In the following, description follows regarding methods of determining specific recommended load data based on the relative strength range or the relative weakness range.

Figure 20:
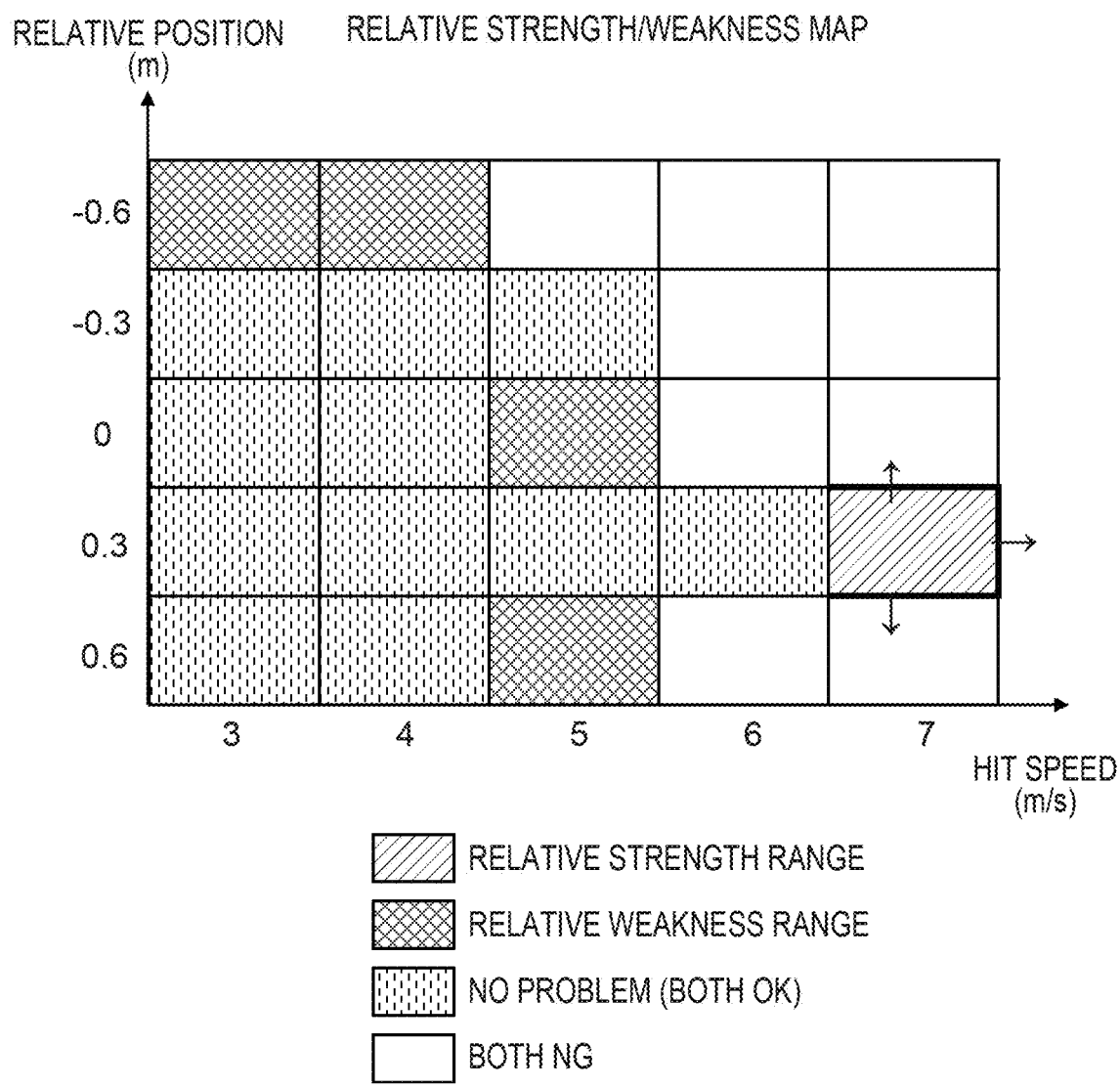
FIG. 20 is a diagram to explain determining recommended load data based on a relative strength/weakness map.

When considering skill improvement, practice that enables broadening of the relative strength range is desirable. Thus in cases in which the recommended load data is determined based on the relative strength range, the determination section 420 is accordingly able to determine the recommended load data from above a boundary (the bold line in FIG. 20) between cells indicating the relative strength range and cells having a lower ball return rate than the prescribed value, as illustrated in FIG. 20. This thereby enables an improvement in ball return rate of the target user to be achieved with respect to loads included in the range of the directions indicated by the arrows in FIG. 20.

Figure 21:
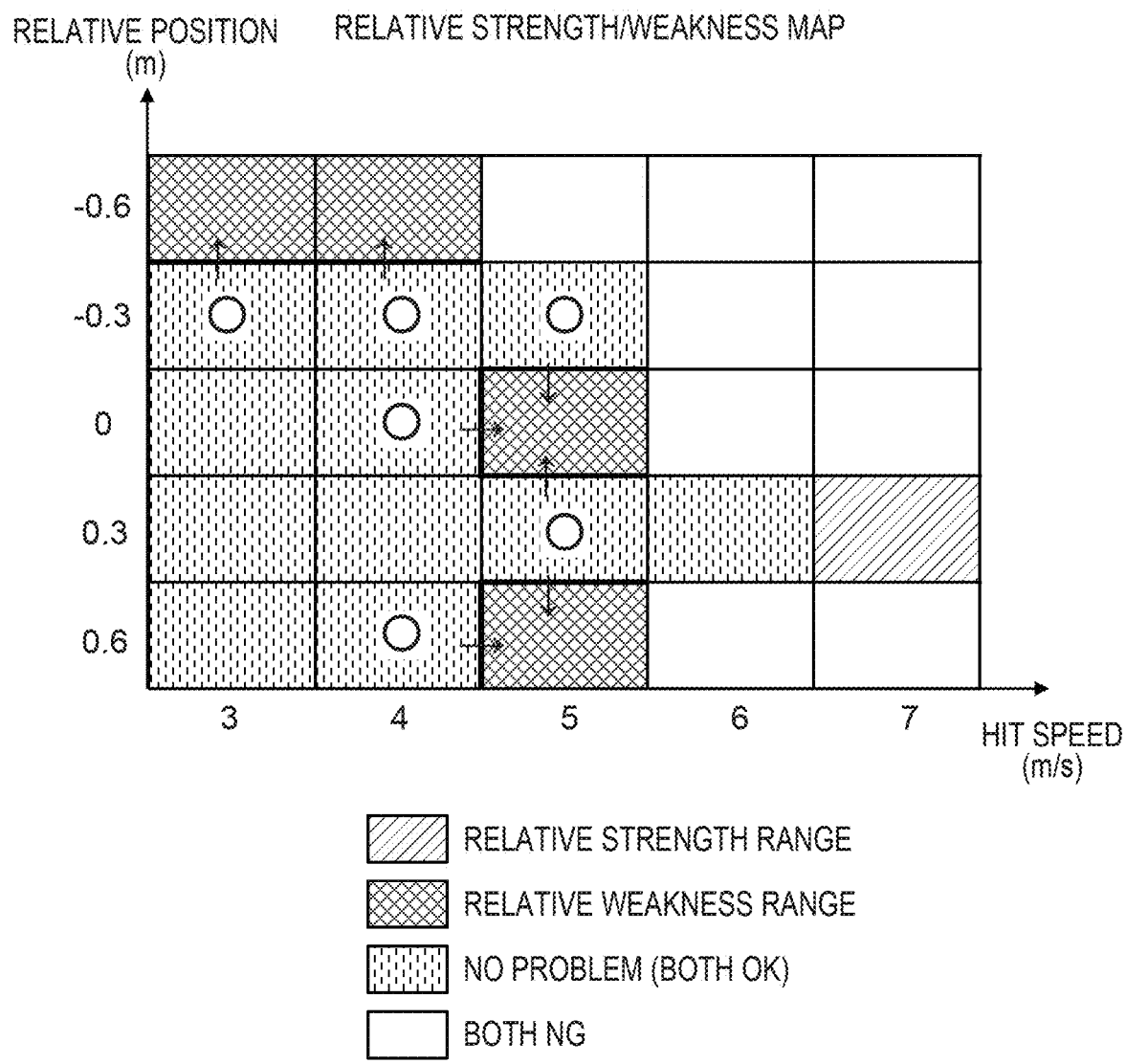
FIG. 21 is a diagram to explain determining recommended load data based on a relative strength/weakness map.

Moreover, a way of practicing with a load having a borderline return ball success or failure is considered to be more advantageous in skill improvement than continuing to practice in a range of load with a low ball return rate for the target user. In cases in which the recommended load data is determined based on the relative weakness range, as illustrated in FIG. 21, the determination section 420 may accordingly determine the recommended load data from a range of cells adjacent to relative weakness cells and having a ball return rate of the prescribed value or higher (cells indicated by the circle marks in FIG. 21). Alternatively, the determination section 420 may accordingly determine the recommended load data from above a boundary (the bold line in FIG. 21) between relative weakness cells and cells having a ball return rate of the prescribed value or higher. The accordingly enables an improvement in ball return rate of the target user to be achieved for a load included in a range of the directions indicated by the arrows in FIG. 21, namely contained in the relative weakness range.

The hardware configuration of the recommended load determining device 410 is similar to the hardware configuration of the recommended load determining device 10 according to the first exemplary embodiment as illustrated in FIG. 3, and so explanation thereof will be omitted. Note that a recommended load determining program for executing recommended load determination processing, described later, is stored in the storage device 36.

Next, description follows regarding operation of the recommended load determining device 410 according to the fourth exemplary embodiment.

Figure 22:
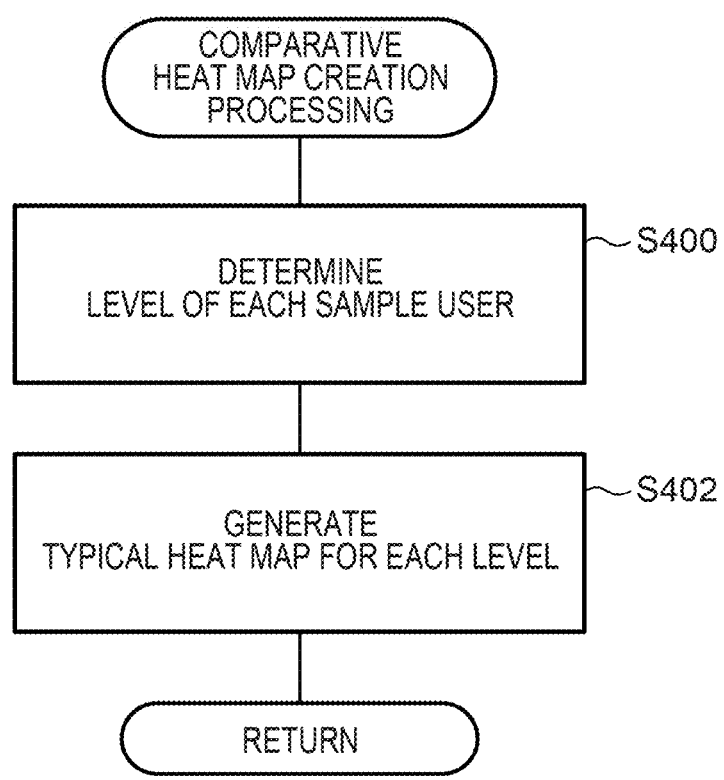
FIG. 22 is a flowchart illustrating an example of a comparison heat map creation processing of the fourth exemplary embodiment.

In the fourth exemplary embodiment, in cases in which affirmative determination is made at step S200 in the recommended load determination processing of the third exemplary embodiment (FIG. 16) and processing has transitioned to the processing of training mode from step S202 onward, a comparison heat map creation processing as illustrated in FIG. 22 is executed after step S212.

In the comparison heat map creation processing illustrated in FIG. 22, at step S400, the training section 416 determines a level of each sample user based on level steps defined according to a proportion of the number of cells having a ball return rate of a prescribed value (for example, 85%) or higher with respect to the total number of cells in the heat map.

Next at step S402, as a comparison heat map, the training section 416 calculates a heat map typical for each level from a heat map calculated for each sample user of the same level, and stores this in the comparison heat map DB 422. The comparison heat map creation processing is then ended, and the recommended load determination processing is also ended.

However, when negative determination is made at step S200 and processing has transitioned to step S214 onward in the practice mode, at step S214 the estimation model 318 determines that generation of the estimation model 318 is complete. In such cases, the acquisition section 412 acquires a strength/weakness instruction of the target user that was input to the recommended load determining device 410 through the input device 38.

Figure 23:
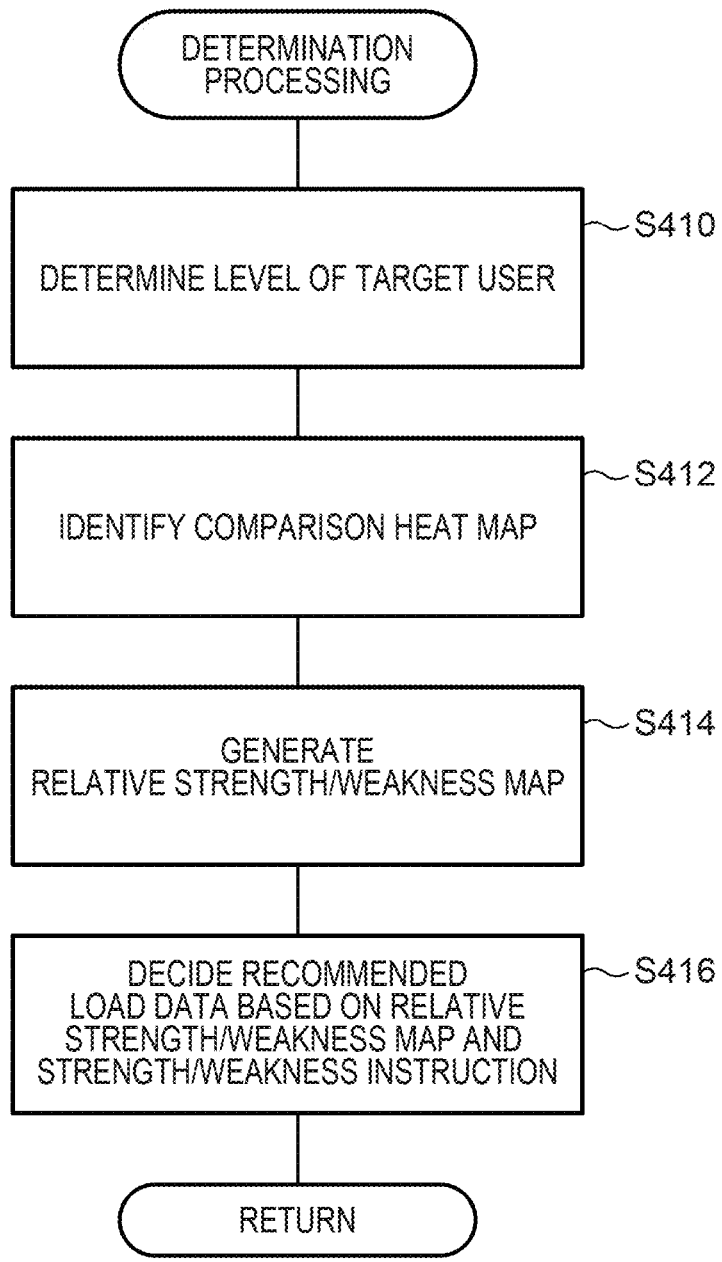
FIG. 23 is a flowchart illustrating an example of determining processing of the fourth exemplary embodiment.

The processing of step S316 to S320 is executed similarly to the recommended load determination processing of the third exemplary embodiment, and at step S321 the determination processing illustrated in FIG. 23 is executed.

In the determination processing illustrated in FIG. 23, at step S410 the determination section 420 determines a level of the target user based on the heat map of the target user as estimated at step S320. Next at step S412, as the comparison heat map, the determination section 420 identifies the typical heat map of the same level as the level of the target user as determined at step S410, or of a level one rank higher, and acquires this from the comparison heat map DB 422.

Next at step S414, the determination section 420 compares values (ball return rates) of each cell in the target user heat map against the comparison heat map, and creates a relative strength/weakness map. Next at step S416, the training section 416 determines the recommended load data based on the relative strength/weakness map created at step S414, and on the strength/weakness instruction acquired by the acquisition section 412. The processing then returns to the recommended load determination processing (FIG. 16).

As described above, in the recommended load determining device according to the fourth exemplary embodiment, a relative strength/weakness map is created in which the relative strength range and the relative weakness range of the target user compared to other users are identified. Due to the recommended load data being determined based on this relative strength/weakness map, from out of the candidate sets of possible load values for recommended load data, a set of load values that is a more advantageous set to skill improvement than in the third exemplary embodiment can be determined as the recommended load data.

Note that although description in the fourth exemplary embodiment is regarding a case in which a relative strength/weakness map is created in which both the relative strength range and the relative weakness range have been identified, there is no limitation thereto. A relative strength map that has identified only the relative strength range may be created, or a relative weakness map that has identified only the relative weakness range may be created. In such cases, in practice mode a strength of the target user may be practiced based on the relative strength map, or a weakness of the target user may be practiced based on the relative weakness map. Moreover, a configuration may be adopted in which a strength/weakness instruction is acquired, and the relative strength map created when "strength" is instructed, and the relative weakness map created when "weakness" is instructed.

In the fourth exemplary embodiment, the determination section may be configured so as to output data for displaying a visualization of a created relative strength/weakness map, relative strength map, or relative weakness map. Adopting such an approach enables target users to objectively ascertain their own relative strength range and relative weakness range for themselves.

Fifth Exemplary Embodiment

Next, description follows regarding a fifth exemplary embodiment. The fifth exemplary embodiment will be described for a case in which, similarly to in the second to the fourth exemplary embodiments, the motor task is to improve the ball return rate in a table tennis rally, the load imparted to the user is a return ball from a table tennis robot, and a motion of the user is a swing to return the ball hit by the table tennis robot. When the objective of the motor task is skill improvement, there are sometimes cases in which there is a desire to improve a skill at the motor task under more precise limitations. For example, in the example of table tennis, rather than simply aiming to improve the ball return rate, there are sometimes cases in which there is a desire to improve the ball return rate for a particular shot type, such as a cut, smash, forehand drive, or the like. Description follows regarding a method of the fifth exemplary embodiment to determine recommended load data that is advantageous to more precise demands on the motor task.

Figure 24:
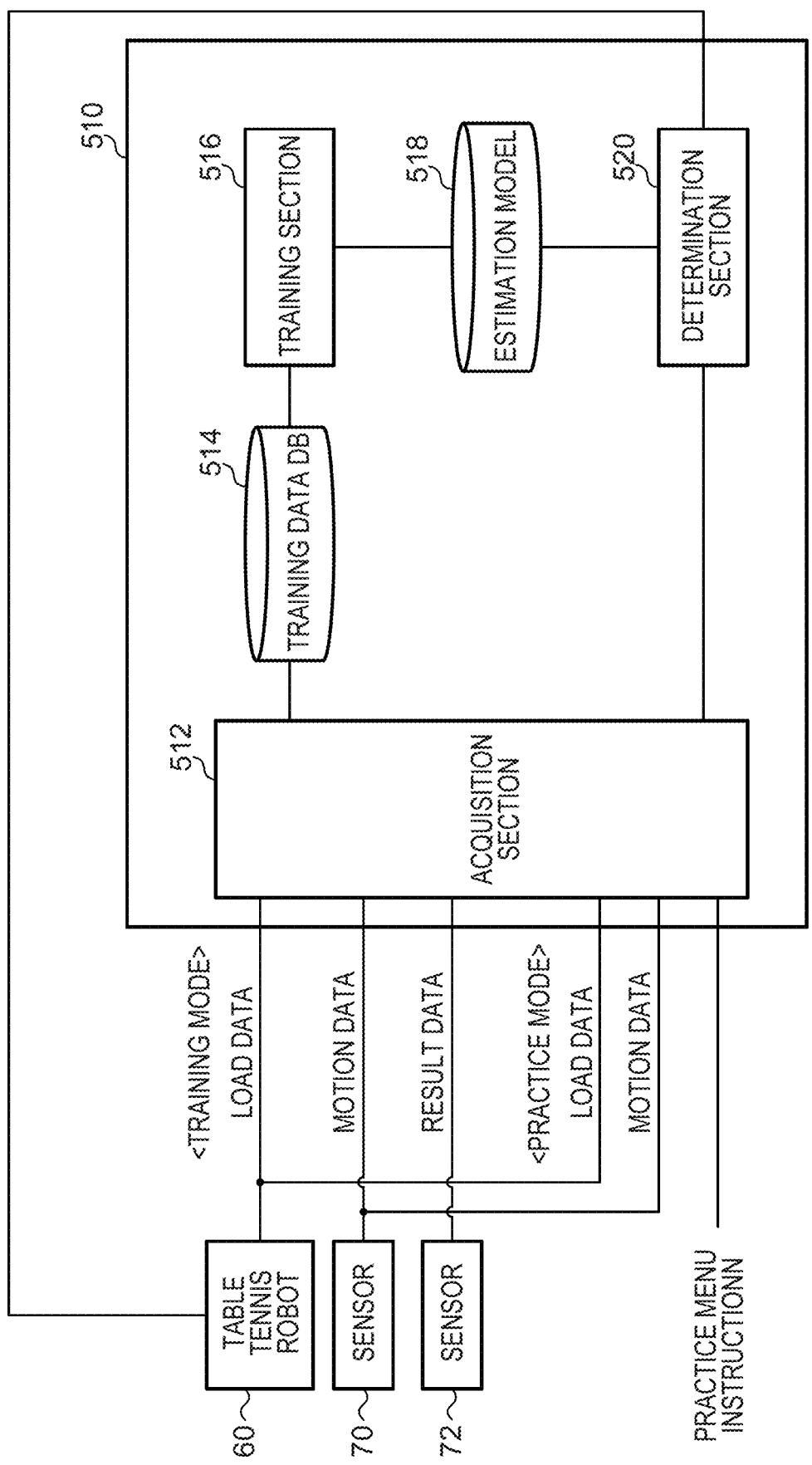
FIG. 24 is a functional block diagram of a recommended load determining device according to a fifth exemplary embodiment.

As illustrated in FIG. 24, a recommended load determining device 510 according to the fifth exemplary embodiment includes, from a functional perspective, an acquisition section 512, a training data DB 514, a training section 516, an estimation model 518, and a determination section 520.

Similarly to the acquisition section 212 according to the second exemplary embodiment, in training mode the acquisition section 512 acquires the load data, the motion data, and the result data, and in practice mode acquires the load data and motion data. For example, the load data is a hit speed, the motion data is the skeleton information of a user, and the result data is a ball return error. Note that similarly to the acquisition section 312 of the third exemplary embodiment or the acquisition section 412 of the fourth exemplary embodiment, the acquisition section 512 may be configured so as to acquire, as plural items of load data, for example, hit speed, ball spin, and relative position. Note that in training mode, motion data and result data is acquired for cases in which a ball is returned by the sample user using an instructed shot type, such as cut, smash, forehand drive, or the like. The data such as illustrated in FIG. 8 or FIG. 13 is accordingly stored in the training data DB 514 for each shot type. Note that "shot type" is an example of a "motion type" of technology disclosed herein.

Furthermore, in practice mode the acquisition section 512 acquires an instruction on a practice menu indicating a shot type the target user wants to practice. This instruction is input to the recommended load determining device 510 through the input device 38.

Figure 25:
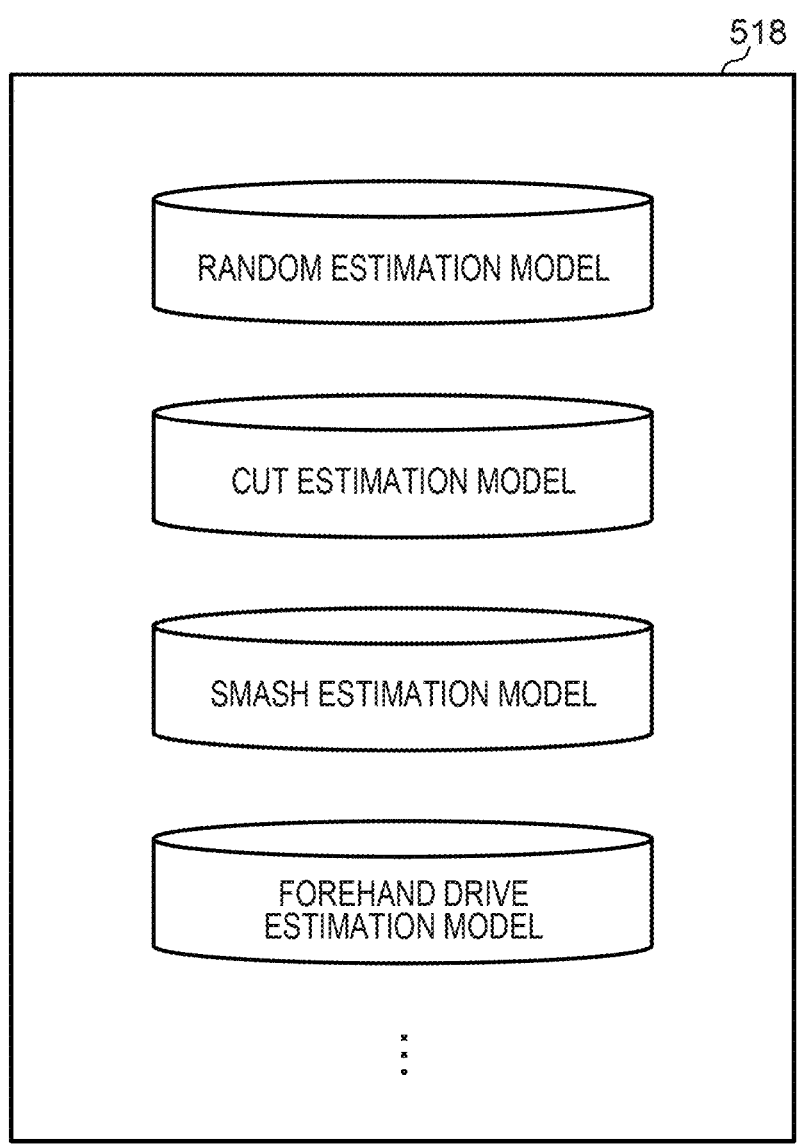
FIG. 25 is a diagram illustrating an example of an estimation model of the fifth exemplary embodiment.

The training section 516 generates the estimation model 518 using the training data for each shot type. The specific method of generating the estimation model 518 is similar to those of the second to the fourth exemplary embodiments. The estimation model 518 is, as illustrated in FIG. 25, accordingly configured by a collection of estimation models for each respective shot type, such as cut, smash, forehand drive, and the like. Note that in the example illustrated in FIG. 25, an estimation model for random generation without limitation for shot type is also included in the estimation model 518.

The determination section 520 uses the shot type estimation model corresponding to the instruction on the practice menu as acquired by the acquisition section 512 from out of the estimation model 518, estimates the capability parameter of the target user, and then determines the recommended load data based on the capability parameter. The specific method of determining the recommended load data based on the capability parameter is similar to those of the second to the fourth exemplary embodiments.

The hardware configuration of the recommended load determining device 510 is similar to the hardware configuration of the recommended load determining device 10 according to the first exemplary embodiment as illustrated in FIG. 3, and so explanation thereof will be omitted. Moreover, the operation of the recommended load determining device 510 according to the fifth exemplary embodiment also differs from the recommended load determination processing of the second to fourth exemplary embodiment only in that the practice menu instruction is acquired, and that the estimation model for the shot type corresponding to the instruction on the practice menu is employed for step S220 of FIG. 10 or for step S320 of FIG. 16, and so detailed explanation thereof will be omitted.

As described above, in the recommended load determining device according to the fifth exemplary embodiment, for example, an estimation model is prepared for each shot type, and the estimation model for the shot type instructed by the target user is employed to estimate the capability parameter of the target user and to determine the recommended load data. This thereby enables recommended load data to be determined that is advantageous to more precise demands for the motor task.

Sixth Exemplary Embodiment

Next, description follows regarding a sixth exemplary embodiment. Similarly to in the second to the fifth exemplary embodiments, description follows for the sixth exemplary embodiment for a case in which the motor task is to improve a ball return rate in a table tennis rally, the load imparted to the user is returning a ball by a table tennis robot, and the motion of the user is a swing to return the ball hit by the table tennis robot. In each of the exemplary embodiments described above, the load data and motion data are input to the estimation model, and the capability parameter of the target user is estimated. This means that, for example, for table tennis, sometimes an excessively large load is imparted to a target user having a poor ball return rate irrespective of their swing being skillful. For example, there is a possibility that a fast ball will be delivered to a target user who has performed diligent practice-swing practice and is already has a good swing, but is unable to follow a fast ball with their eyes. Or in the opposite situation, sometimes there are cases in which the load is not sufficient for a target user who has a good ball return rate using an unorthodox swing not considered a good swing. In the sixth exemplary embodiment, description follows regarding a method of correcting load is such cases and determining recommended load data advantageous to skill improvement.

Figure 26:
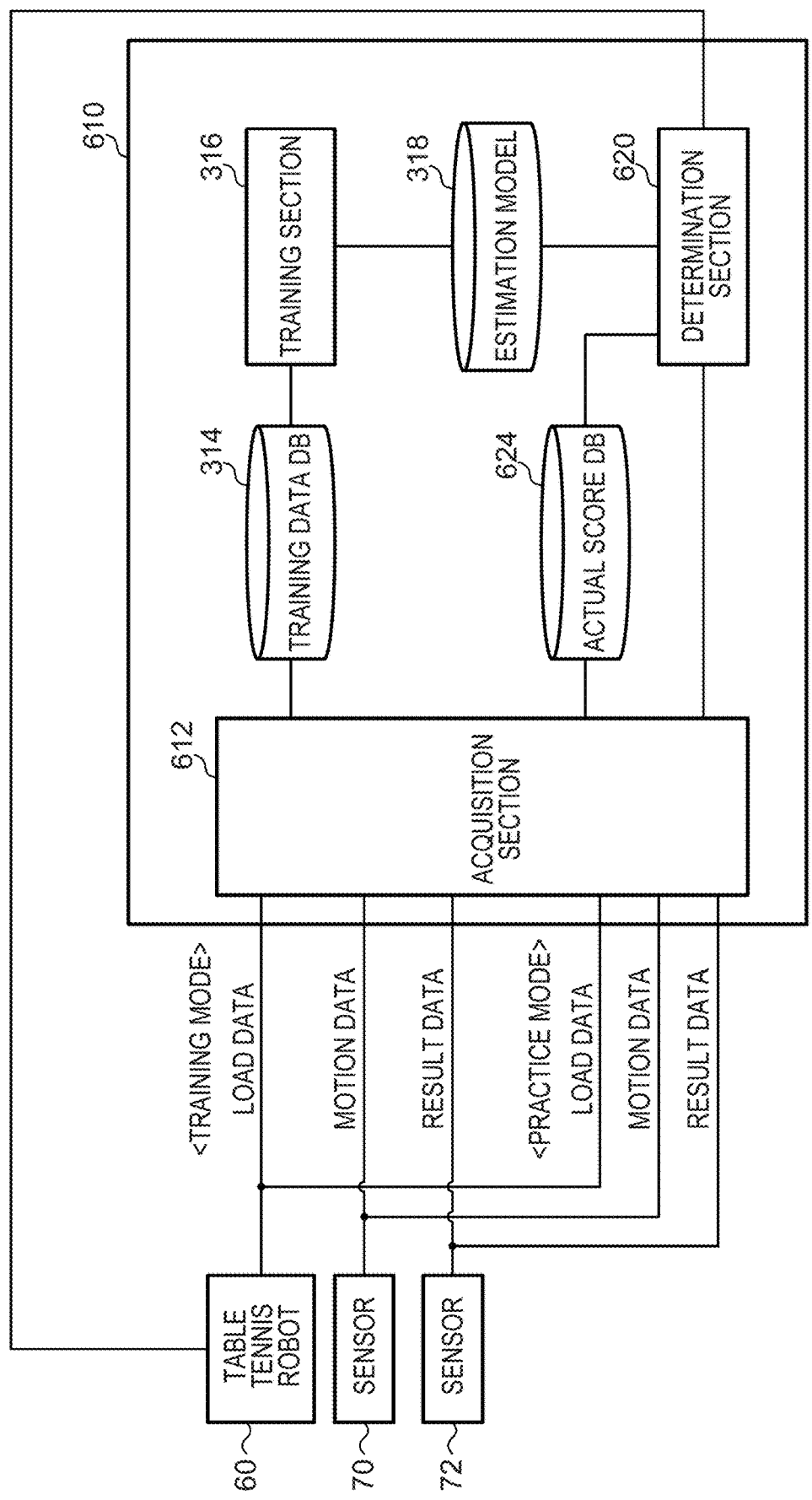
FIG. 26 is a functional block diagram of a recommended load determining device according to a sixth exemplary embodiment.

As illustrated in FIG. 26, a recommended load determining device 610 according to the sixth exemplary embodiment includes, from a functional perspective, an acquisition section 612, an actual score DB 624, a training data DB 314, a training section 316, an estimation model 318, and a determination section 620.

Similarly to the acquisition section 312 according to the third exemplary embodiment, in training mode the acquisition section 612 acquires plural items of load data, motion data, and result data. In practice mode, in addition to the plural items of load data and the motion data, the acquisition section 612 also acquires result data as a measured parameter of a motion result. For example, the plural items of load data are hit speed, ball spin, and relative position, the motion data is skeleton information of a user, and the result data is ball return error. The acquisition section 612 stores result data acquired in the practice mode for each attempt, for example in the actual score DB 624 such as illustrated in FIG. 27.

In cases in which the capability of the target user as evaluated by the result data is lower than the capability of the target user as evaluated by the capability parameter output by the estimation model 318, the determination section 620 determines the recommended load data such that the burden on the target user is made smaller. Moreover, in cases in which the capability of the target user as evaluated by the result data is higher than the capability of the target user as evaluated by the capability parameter output by the estimation model 318, the determination section 620 determines the recommended load data such that the burden on the target user is made greater.

More specifically, similarly to the determination section 320 of the third exemplary embodiment, the determination section 620 uses the estimation model 318 to estimate a heat map as the capability parameter of the target user, and then identifies cells from the heat map for determining the recommended load data. The determination section 620 calculates an actual score ball return rate from the ball return error in a prescribed number of past attempts stored in the actual score DB 624. In cases in which the actual score ball return rate is a lower limit threshold (for example, 85%) or lower, there is a possibility that the estimated ball return rate stored in each cell of the estimated heat map is a value higher than the actual score ball return rate corresponding to the actual capability of the target user, and that cells of range of a load with a high burden for the target user is identified. The determination section 620 accordingly corrects the cells identified from the heat map in a direction of lower load (decrease direction). However, in cases in which the actual score ball return rate is an upper limit threshold (for example, 95%) or higher, there is a possibility that the estimated ball return rate stored in each cell of the estimated heat map is a value lower than the actual score ball return rate corresponding to the actual capability of the target user, and that cells in a range of load with a lower burden for the target user might be identified. The determination section

620 accordingly corrects the cells identified from the heat map in a direction of higher load (increase direction).

Figure 28:
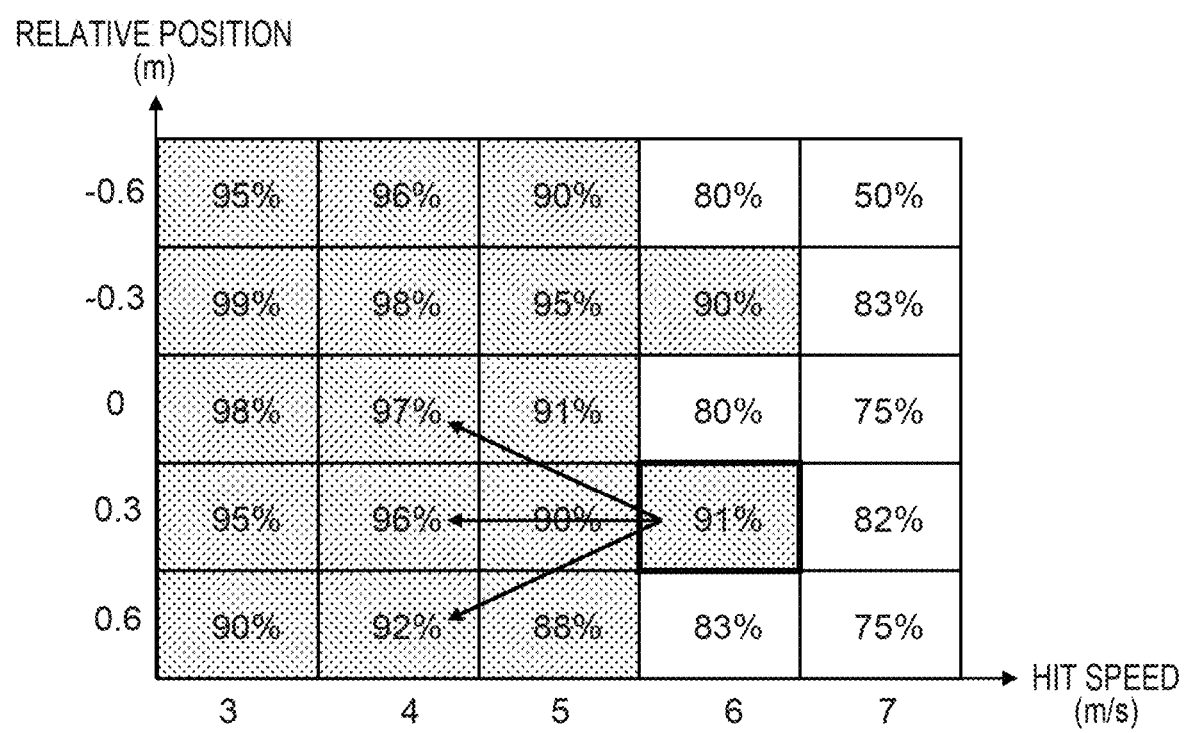
FIG. 28 is a diagram to explain load reduction directions.
Figure 29:
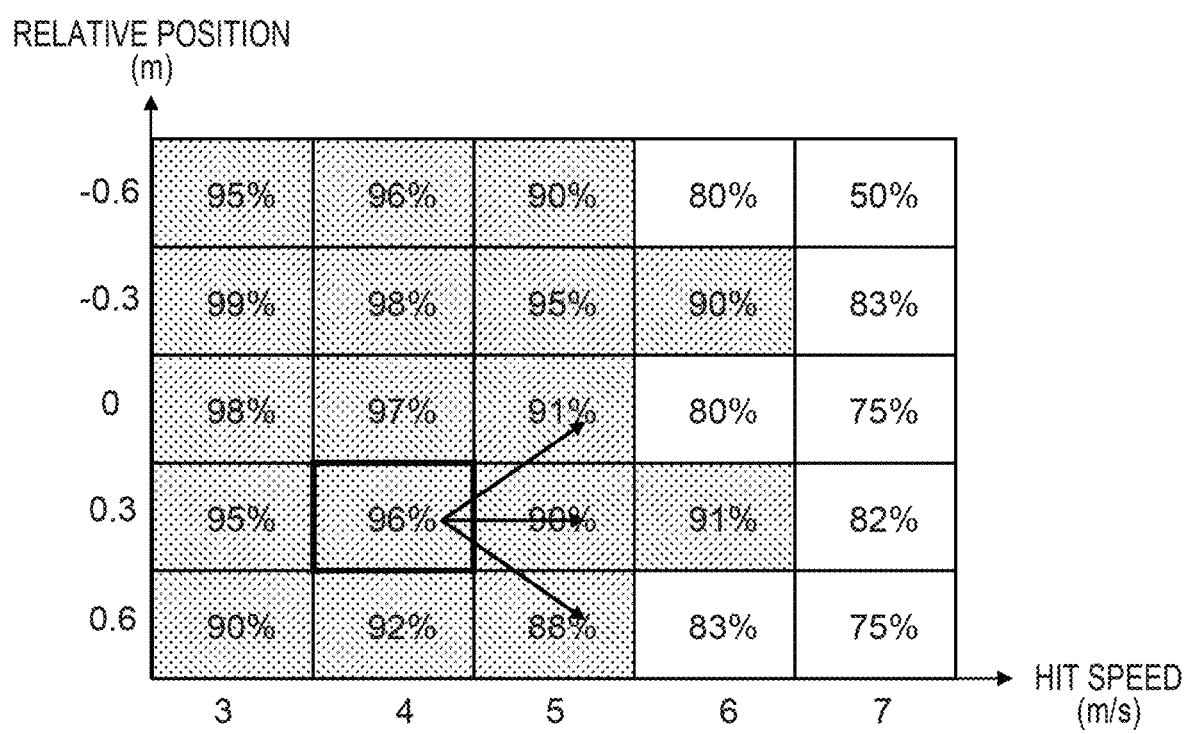
FIG. 29 is a diagram to explain load increase directions.

The load decrease direction is, for example as illustrated in FIG. 28, directions toward cells of improved estimated ball return rates as illustrated by the arrows in FIG. 28 with reference to the load contained in the cell marked with a bold box in FIG. 28. The load increase direction is, for example as illustrated in FIG. 29, directions towards cells of lowered estimated ball return rates as illustrated by the arrows in FIG. 29 with reference to the load contained in the cell marked with a bold box in FIG. 29. For example, the determination section 620 may identify a cell in the heat map that is nearest to the identified cell in the increase direction or the decrease direction, and determine a set of the values of loads included in the range of the identified cell as the recommended load data.

The hardware configuration of the recommended load determining device 610 is similar to the hardware configuration of the recommended load determining device 10 according to the first exemplary embodiment as illustrated in FIG. 3, and so explanation thereof will be omitted. Note that a recommended load determining program for executing recommended load determination processing, described later, is stored in the storage device 36.

Next, description follows regarding operation of the recommended load determining device 610 according to the sixth exemplary embodiment.

In the recommended load determination processing of the sixth exemplary embodiment, similarly to in the recommended load determination processing of the third exemplary embodiment (FIG. 16), transition is made to the processing of the practice mode for step S214 onward when a negative determination is made at step S200. Then when determination at step S214 is that generation of the estimation model 318 is complete, the determination processing illustrated in FIG. 30 is executed instead of steps S316 to S321.

Figure 30:
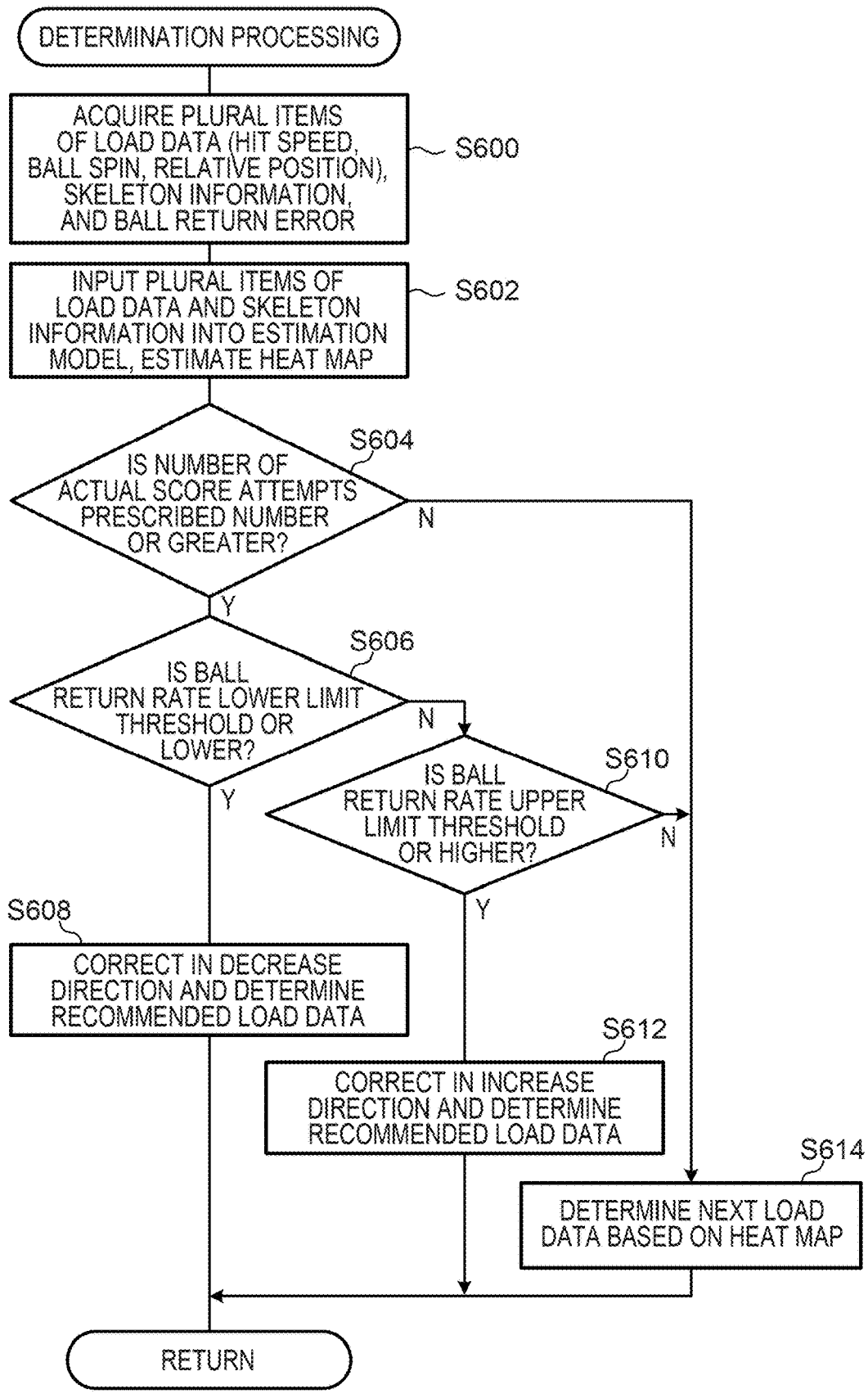
FIG. 30 is a flowchart illustrating an example of determining processing of the sixth exemplary embodiment.

At step S600 in the determination processing illustrated in FIG. 30, the acquisition section 612 acquires plural items of load data (hit speed, ball spin, and relative position), and the skeleton information, and stores these in the training data DB 314. The acquisition section 612 also acquires the ball return error and stores this in the actual score DB 624. Next, at step S602, the determination section 620 inputs the plural items of load data and the skeleton information into the estimation model 318, estimates the heat map for the target user, and then identifies a cell from the heat map for determining the recommended load data.

Next at step S604, the determination section 620 determines whether or not result data (ball return error) for a prescribed number of attempts or greater is stored in the actual score DB 624. Processing transitions to step S606 when these are stored, and processing transitions to step S614 when these are not stored.

At step S606, the determination section 620 determines whether or not the ball return rate as calculated form the ball return error of the prescribed number of past attempts stored in the actual score DB 624 is a lower limit threshold (for example, 85%) or lower. Processing transitions to step S608 in cases in which the ball return rate is the lower limit threshold or lower, and processing transitions to step S610 in cases in which the lower limit threshold is exceeded. At step S608, the determination section 620 identifies the cell identified from the heat map to correct in a decrease direction, and then determines the recommended load data as a set of values of load contained in the range of the identified cell.

However, at step S610 the determination section 620 determines whether or not the ball return rate is the upper limit threshold (for example 95%) or higher. Processing transitions to step S612 in cases in which the ball return rate is the upper limit threshold or higher, and processing transitions to step S614 in cases less than the upper limit threshold. At step S612, the determination section 620 identifies the cell identified from the heat map to correct in an increase direction, and then determines the recommended load data as a set of values of the load contained in the range of the identified cell.

At step S614, the determination section 620 determines the recommended load data as a set of values of the load contained in the range of the cell identified at step S602. The processing then returns to the recommended load determination processing (FIG. 16).

As described above, in the recommended load determining device according to the sixth exemplary embodiment, the recommended load data for determination is corrected in the increase direction or the decrease direction according to the capability of the target user as indicated by the actual scores. This thereby enables recommended load data to be determined that is advantageous to skill improvement according to the actual scores of the target user.

Note that although the sixth exemplary embodiment has been described for a case in which the load is corrected in the increase direction for a target user having a good ball return rate although not a good swing, there is no limitation thereto. For example, a configuration may be adopted in which the correction in the increase direction is not performed in cases in which the motor task is to enable a good swing to be performed. In such cases, although a load that is low for the target user is imparted, there is no problem from not performing a correction in the increase direction because this is practice performed at low load until the quality of the swing is improved.

Figure 31:
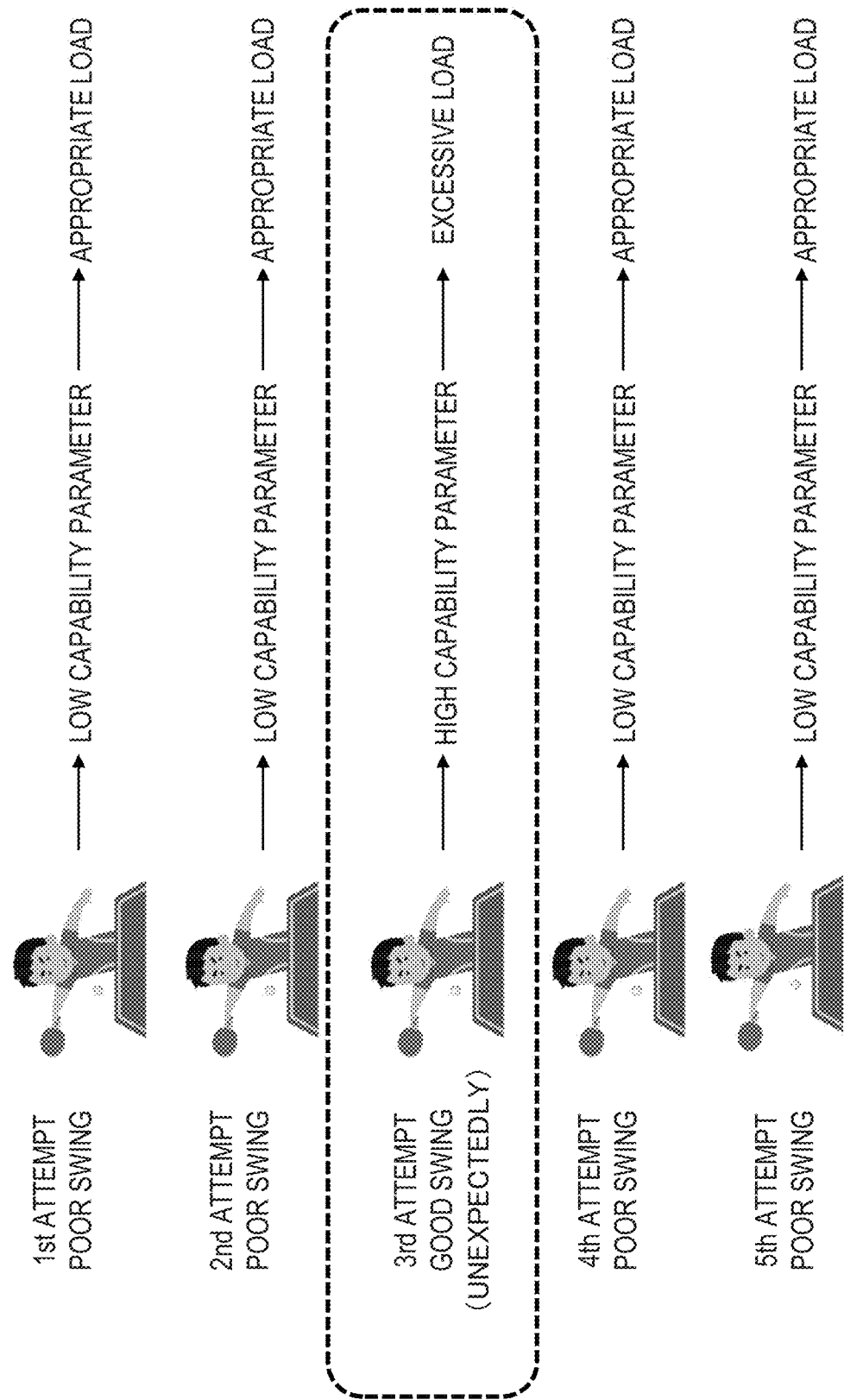
FIG. 31 is a diagram to explain unexpected fluctuations in load.

Moreover, in the exemplary embodiment described above a case is described in which the recommended load data for the next attempt is determined based on the load data imparted for the current attempt and the motion data for this the load data. In such cases, as illustrated in FIG. 31, when the swing is usually poor but by chance the swing was good for a single attempt, this will sometimes result in an excessive load being imparted for the next attempt. The example of FIG. 31 illustrates an example in which there is a poor swing at attempts 1, 2, 4, and 5, but a good swing was achieved by chance for the 3rd attempt. In such cases a low capability parameter is estimated for the poor swing, and recommended load data appropriate to the target user is determined. However, due to a high capability parameter being estimated for the good swing, recommended load data having a high burden for the target user is determined.

Figure 32:
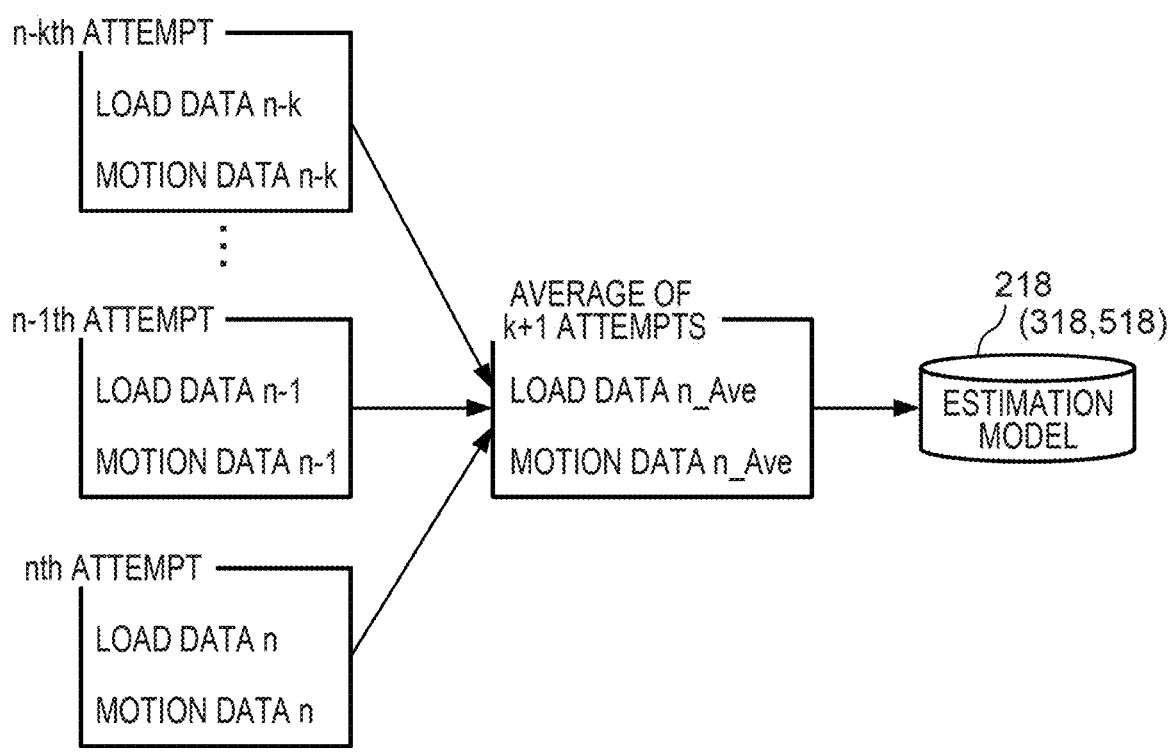
FIG. 32 is a diagram to explain averaging of input to an estimation model.

In order to suppress such unexpected fluctuations in the load data, an average is taken across k+1 instances of load data and motion data for k+1 past attempts ($n^{th}$ attempt, $n-1^{th}$ attempt, . . . , $n-k^{th}$ attempt), as illustrated in FIG. 32. Then the capability parameter for the $n^{th}$ attempt may be estimated by inputting the averaged load data n_Ave and motion data n_Ave into the estimation model.

Figure 33:
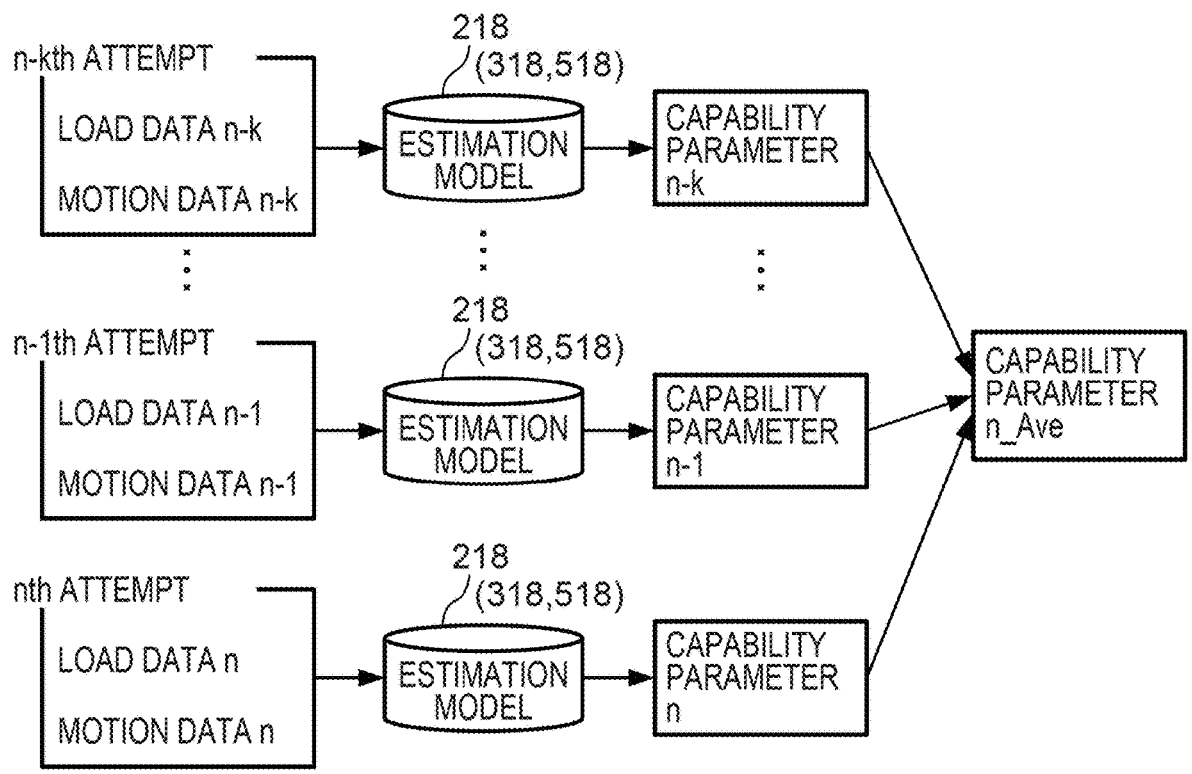
FIG. 33 is a diagram to explain averaging of output from an estimation model.

Moreover, as illustrated in FIG. 33, a configuration may be adopted in which an average is taken across k+1 instances of the capability parameter as estimated for k+1 past attempts ($n^{th}$ attempt, $n-1^{th}$ attempt, . . . , $n-k^{th}$ attempt), so as to determine the recommended load data from the averaged capability parameter n_Ave. Moreover, the recommended load data determined based on each of the k+1 individual capability parameters may be averaged, and this employed as the final recommended load data.

Figure 34:
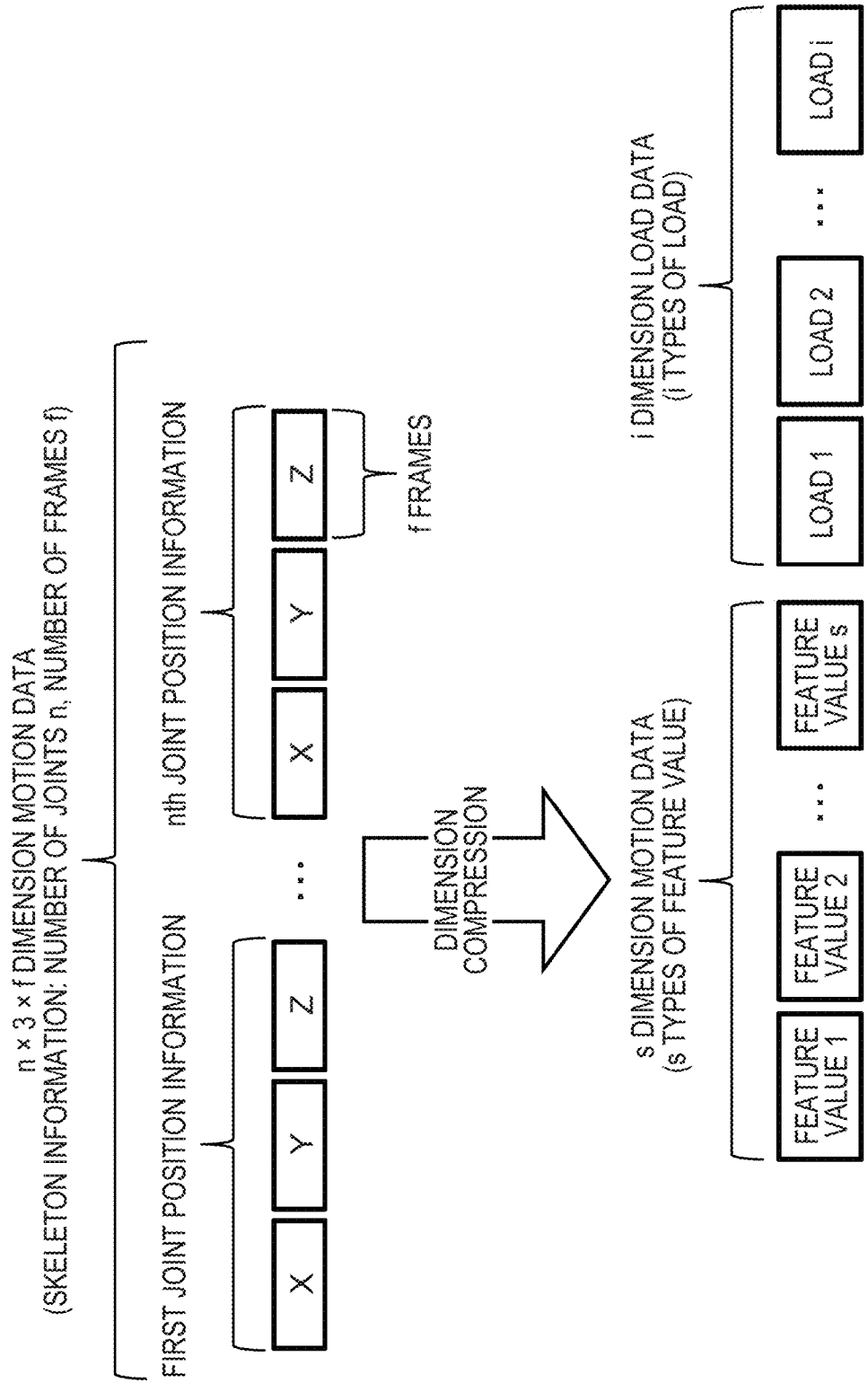
FIG. 34 is a diagram to explain dimension compression of motion data.

Each of the exemplary embodiments described above have been described for cases in which, for example as illustrated in FIG. 14, the capability parameter is estimated by inputting the load data and the motion data into an estimation model realized by a neural network or the like. As described above, in cases such as when skeleton information is employed as the motion data, there is a possibility that there is too great a difference between the dimensionality of the motion data and the dimensionality of the load data, with this difference in dimensionality having an influence that leads biased training when the estimation model is being trained. Thus, as illustrated in FIG. 34, training data may be employed after compressing the dimensionality of the motion data such that the dimensionality of the motion data is at the same level of dimensionality as the dimensionality of the load data. In such cases dimension compression of the motion data is performed when estimating the capability parameter similarly to when performing training. Note that the reference to being at the same level of dimensionality means that a difference between the dimensionality of the load data and the dimensionality of the motion data is a number of dimensions that falls within a prescribed range. In the example illustrated in FIG. 34, the skeleton information that is the motion data has a number of joints n, 3 coordinate values to express each joint, and f as the number of frames of images for a single motion unit, and so the number of dimensions of the motion data is n×3×f. s types of feature values are extracted from the motion data so as to make this number of dimensions the number of dimensions s at the same level of dimensionality as the number of dimensions i of the load data, and the post dimensionality compressed motion data is employed.

Description follows regarding an example of a method to compress the dimensionality of the motion data. For example, a matrix such that illustrated in FIG. 35 is created from the motion data for the plural sample users. Actual coordinate values of skeleton information are input to the shaded portion in FIG. 35. Main component analysis is performed on this matrix and, for example, a cumulative contribution ratio of the main components is found, and highest ranking s individual main component are identified. Then as illustrated in FIG. 36, values are calculated of the motion data representing each swing mapped onto each of the identified main components P1, P2, . . . , Ps. The values mapped onto each of the main components are input to the shaded portion of FIG. 36. Adopting such an approach enables the n×3×f dimension motion data to be dimensionally compressed to s dimensions.

Moreover, as another method of dimension compression, the motion data may be featurized so as to express a quality of swing based on knowledge information related to the motion and analysis of the motion data. For example, when there is knowledge that a height of the elbow remains constant in a swing of a skillful person, a distribution of elbow heights is extracted as a feature value from the motion data. Moreover, when there is knowledge that a trajectory of a swing is smooth for a skillful person, analysis such as, for example, taking a differential or the like is performed on a trajectory indicated by the motion data, and an index to indicate the smoothness of trajectory is extracted as a feature value. As illustrated in FIG. 37, the motion data representing each swing is then featurized. The feature values extracted from the motion data related to each feature are input to the shaded portions of FIG. 37.

Moreover, the third to the sixth exemplary embodiment have been described for examples in which the recommended load is determined for a motor task of improving a ball return rate using a table tennis robot, however, there is no limitation thereto. As explained toward the end of the second exemplary embodiment, a motor task of improving a safe hit rate using a batting machine and a motor task of improve walking in rehabilitation using a treadmill as in the examples given in the first exemplary embodiment, may similarly be implemented as concrete exemplary embodiments in the third to the sixth exemplary embodiments.

Moreover, although description of each of the exemplary embodiments is of cases in which the functional section that functions in the training mode and the functional section that functions in training practice mode are implemented by the same computer, there is no limitation thereto. A capability parameter estimation model training device including an acquisition section and a training section, and a recommended load determining device including an acquisition section and a determining section, may each be implemented by separate computers.

Moreover, the recommended load determination processing executed in each of the exemplary embodiments by a CPU reading software (a program) may be executed by various processors other than an CPU. Examples of such processors include programmable logic devices (PLD) that allow circuit configuration to be modified post-manufacture, such as a field-programmable gate array (FPGA), and dedicated electric circuits, these being processors including a circuit configuration custom-designed to execute specific processing, such as an application specific integrated circuit (ASIC). Moreover, the recommended load determination processing may be executed by any one of these various types of processors, or may be executed by a combination of two or more of the same type or different types of processors (such as plural FPGAs, or a combination of a CPU and an FPGA). The hardware structure of these various types of processor is more specifically an electric circuit combining circuit elements such as semiconductor elements.

Moreover, although description of each of the exemplary embodiments is of embodiments in which the recommended load determining program is pre-stored (installed) on a storage device, there is no limitation thereto. The program may, for example, be provided in a format stored on a storage medium such as a CD-ROM, DVD-ROM, Blu-ray Disc, USB memory, or the like. Moreover, an embodiment may be configured in which the program is downloaded from an external device over a network.

All publications, patent applications and technical standards mentioned in the present specification are incorporated by reference in the present specification to the same extent as if each individual publication, patent application, or technical standard was specifically and individually indicated to be incorporated by reference.

EXPLANATION OF REFERENCE NUMERALS 10, 210, 310, 410, 510, 610 recommended load determining device
12, 212, 312, 412, 512, 612 acquisition section
14, 214, 214A, 214B, 314, 514 training data DB
16, 216, 316, 416, 516 training section
18, 218, 318, 518 estimation model
20, 220, 320, 420, 520, 620 determination section
422 comparison heat map DB
624 actual score DB
32 CPU 34 memory
36 storage device
38 input device
40 output device
42 storage medium reading device
44 communication I/F
46 bus
60 table tennis robot
72 sensor

The invention claimed is:

1. A recommended load determining device utilizing an estimation model that outputs a parameter related to a capability of a user calculated based on load data expressing a load imparted to the user and on motion data expressing motion of a single motion unit of the user under the load, the recommended load determining device comprising:
   an acquisition section that acquires load data expressing a load imparted to a target user who is a target for determining a recommended load, and motion data expressing motion of a single motion unit of the target user under the load; and
   a determination section that determines recommended load data expressing a recommended load for the target user based on a parameter related to the capability of the target user as output from the estimation model by inputting the acquired load data and the acquired motion data into the estimation model,
wherein:
   the parameter related to the capability output by the estimation model is a parameter expressing a relationship between the load and a success expectation value for the motion; and
   the determination section determines the recommended load data based on the parameter related to the capability for the target user.

2. The recommended load determining device of claim 1, wherein the motion data is displacement data of a particular location of the user or of an implement held when the user is performing the motion, muscle activity quantity data of the user, or differentiated data or integrated data of the displacement data or the muscle activity quantity data.

3. The recommended load determining device of claim 2, wherein the displacement data of the particular location of the user is time series data of skeleton information of the user.

4. The recommended load determining device of claim 1, wherein:
   the parameter related to the capability output by the estimation model is load limit data expressing a value of the load at a maximum burden for the user from within a range of values of the load for one load item when an expectation of success for the motion is higher than a prescribed standard; and
   the determination section determines the load limit data for the target user as the recommended load data.

5. The recommended load determining device of claim 1, wherein:
   the parameter expressing a relationship between the load and the success expectation value for the motion for the target user is a parameter to identify a graph expressing a relationship between a value of the load for one load item and the success expectation value; and
   the determination section determines, as the recommended load data, load limit data expressing a value of the load for a maximum burden for the target user from within a range of values of the load in the graph for which the expectation of success is higher than a prescribed standard.

6. The recommended load determining device of claim 1, wherein:
   the parameter expressing the relationship between the load and the success expectation value for the motion for the target user is a parameter to identify a heat map expressing a relationship between values of the load for a plurality of load items and the success expectation value; and
   the determination section determines, as the recommended load data, a set of values of load in the heat map for which the success expectation is higher than a prescribed standard.

7. The recommended load determining device of claim 6, wherein the determination section outputs data to display a visualization of the heat map.

8. The recommended load determining device of claim 6, wherein the determination section is configured so as to be able to utilize a comparison heat map, and creates a relative strength map that identifies a relative strength range that is a range of a set of values of the load for which the success expectation of the target user is higher in a comparison to the comparison heat map, or creates a relative weakness map that identifies a relative weakness range that is a range of a set of values of the load for which the success expectation of the target user is lower in a comparison to the comparison heat map, and determines a set of values of load in the relative strength range or in the relative weakness range as the recommended load data.

9. The recommended load determining device of claim 8, wherein:
   the comparison heat map is prepared for separate levels of the user; and
   the determination section utilizes the comparison heat map for the user at a level equivalent to a level of the target user or at a level that is above the level of the target user and that is a level nearest to the level of the target user.

10. The recommended load determining device of claim 8, wherein:
    the acquisition section further acquires an instruction of strength or weakness for the target user; and
    the determination section creates the relative strength map in cases in which the strength instruction was acquired, and creates the relative weakness map in cases in which the weakness instruction was acquired.

11. The recommended load determining device of claim 8, wherein the determination section outputs data to display a visualization of at least one out of the relative strength map or the relative weakness map.

12. The recommended load determining device of claim 1, wherein:
    the estimation model is prepared for each type of the motion;
    the acquisition section acquires an instruction for one of the types from the target user; and
    the determination section determines the recommended load data using the estimation model corresponding to the instructed type.

13. The recommended load determining device of claim 1, wherein:
    the acquisition section acquires a plurality of sets of a set of the load data and the motion data; and
    the determination section inputs the estimation model with load data resulting from averaging the plurality of the load data and with motion data resulting from averaging the plurality of the motion data.

14. The recommended load determining device of claim 1, wherein:
the acquisition section acquires a plurality of sets of a set of the load data and the motion data; and
the determination section averages a parameter related to the capability obtained by each set of the load data and the motion data being input to the estimation model, and determines the recommended load data based on the averaged parameter.

15. The recommended load determining device of claim 1, wherein:
the acquisition section acquires a plurality of sets of a set of the load data and the motion data; and
the determination section computes a plurality of recommended load data based on a parameter related to the capability obtained by each of the sets of the load data and the motion data being input to the estimation model, and further finally determines the recommended load data by averaging the plurality of recommended load data.

16. The recommended load determining device of claim 1, wherein:
the acquisition section acquires a set of the load data and the motion data and a measured parameter related to an actual motion result corresponding to the set; and
the determination section determines the recommended load data so as to have a smaller burden on the target user in cases in which a capability of the target user as evaluated by the acquired measured parameter is lower than a capability of the target user as evaluated by the parameter as output from the estimation model.

17. The recommended load determining device of claim 1, wherein the determination section outputs the recommended load data to a load imparting device that imparts the load to the target user as data for controlling the load imparting device.

18. The recommended load determining device of claim 1, wherein the determination section outputs data to display a latest of the recommended load data at a prescribed time interval.

19. The recommended load determining device of claim 1, further comprising a training section that generates the estimation model by learning correspondences of the load data and the motion data with respect to a parameter related to a capability of the user as calculated based on the load data and the motion data.

20. The recommended load determining device of claim 19, wherein to generate the estimation model the training section employs the motion data that has been compressed such that a difference between a number of dimensions of the load data and a number of dimensions of the motion data is within a prescribed range.

21. A capability parameter estimation model training device comprising:
an acquisition section that acquires load data expressing a load imparted to a user, motion data indicating motion of a single motion unit of the user under the load, and result data accompanying the motion; and
a training section that learns correspondences of the load data and the motion data with respect to a parameter related to a capability of the user as calculated based on the load data and the result data so as to generate an estimation model that outputs a parameter related to a capability of a target user, who is a target for determining a recommended load, on being input with the load data and the motion data for the target user,
wherein:
the parameter related to the capability output by the estimation model is a parameter expressing a relationship between the load and a success expectation value for the motion; and
the determination section determines the recommended load data based on the parameter related to the capability for the target user.

22. A recommended load determining method comprising:
preparing an estimation model that outputs a parameter related to a capability of a user calculated based on load data expressing a load imparted to the user and on motion data expressing motion of a single motion unit of the user under the load;
an acquisition section acquiring load data expressing a load imparted to a target user who is a target for determining a recommended load and on motion data expressing motion of a single motion unit of the target user under the load; and
a determination section determining recommended load data expressing a recommended load for the target user based on a parameter related to the capability of the target user as output from the estimation model by inputting the acquired load data and the acquired motion data into the estimation model,
wherein:
the parameter related to the capability output by the estimation model is a parameter expressing a relationship between the load and a success expectation value for the motion; and
the determination section determines the recommended load data based on the parameter related to the capability for the target user.

23. A non-transitory storage medium storing a recommended load determining program causing a computer to function as a recommended load determining device that utilizes an estimation model that outputs a parameter related to a capability of a user calculated based on load data expressing a load imparted to the user and on motion data expressing motion of a single motion unit of the user under the load, wherein the recommended load determining program causes the computer to function as:
an acquisition section that acquires load data expressing a load imparted to a target user who is a target for determining a recommended load, and motion data expressing motion of a single motion unit of the target user under the load; and
a determination section that determines recommended load data expressing a recommended load for the target user based on a parameter related to the capability of the target user as output from the estimation model by inputting the acquired load data and the acquired motion data into the estimation model,
wherein:
the parameter related to the capability output by the estimation model is a parameter expressing a relationship between the load and a success expectation value for the motion; and
the determination section determines the recommended load data based on the parameter related to the capability for the target user.

* * * * *